(12) United States Patent
Reicher et al.

(10) Patent No.: US 10,592,688 B2
(45) Date of Patent: *Mar. 17, 2020

(54) SYSTEM AND METHOD OF PROVIDING DYNAMIC AND CUSTOMIZABLE MEDICAL EXAMINATION FORMS

(71) Applicant: MERGE HEALTHCARE SOLUTIONS INC., Hartland, WI (US)

(72) Inventors: Murray A. Reicher, Rancho Santa Fe, CA (US); Evan K. Fram, Paradise Valley, AZ (US)

(73) Assignee: MERGE HEALTHCARE SOLUTIONS INC., Hartland, WI (US)

( * ) Notice: Subject to any disclaimer, the term of this patent is extended or adjusted under 35 U.S.C. 154(b) by 363 days.

This patent is subject to a terminal disclaimer.

(21) Appl. No.: 15/292,014

(22) Filed: Oct. 12, 2016

(65) Prior Publication Data
US 2017/0039350 A1    Feb. 9, 2017

Related U.S. Application Data

(63) Continuation of application No. 13/768,765, filed on Feb. 15, 2013, now Pat. No. 9,501,627, which is a
(Continued)

(51) Int. Cl.
*G06F 21/62* (2013.01)
*G06F 17/24* (2006.01)
(Continued)

(52) U.S. Cl.
CPC ........ *G06F 21/6245* (2013.01); *G06F 19/321* (2013.01); *G06F 19/324* (2013.01);
(Continued)

(58) Field of Classification Search
CPC .. G06F 21/6245; G06F 19/324; G06F 17/243; G06F 19/321; G16H 15/00;
(Continued)

(56) References Cited

U.S. PATENT DOCUMENTS 4,672,683 A    6/1987 Matsueda
5,123,056 A    6/1992 Wilson
(Continued)

FOREIGN PATENT DOCUMENTS

WO    WO 2007/131157    11/2007

OTHER PUBLICATIONS

US 7,801,341 B2, 09/2010, Fram et al. (withdrawn)
(Continued)

*Primary Examiner* — Christopher L Gilligan
(74) *Attorney, Agent, or Firm* — Michael Best & Friedrich LLP

(57) ABSTRACT

A system and method of providing dynamic and customizable medical forms is disclosed. In certain specific embodiments, these dynamic and customizable medical forms may be automatically presented to users based on a predefined series of rules which allow multiple users having different roles in the clinical process to collaborate and contribute to a medical examination report, while at the same time maintaining an independent record of what was contributed and by whom it was contributed.

16 Claims, 23 Drawing Sheets

Related U.S. Application Data continuation of application No. 12/622,404, filed on Nov. 19, 2009, now Pat. No. 8,380,533.

(60) Provisional application No. 61/116,191, filed on Nov. 19, 2008.

(51) Int. Cl.

| | | |
|---|---|---|
| *G16H 10/20* | (2018.01) | |
| *G16H 15/00* | (2018.01) | |
| *G06F 19/00* | (2018.01) | |
| *G06Q 10/10* | (2012.01) | |
| *G06Q 50/22* | (2018.01) | |
| *G06Q 50/24* | (2012.01) | |
| *G06F 40/174* | (2020.01) | |
| *G16H 10/60* | (2018.01) | |

(52) U.S. Cl.
CPC .......... *G06F 40/174* (2020.01); *G06Q 10/10* (2013.01); *G06Q 50/22* (2013.01); *G06Q 50/24* (2013.01); *G16H 10/20* (2018.01); *G16H 15/00* (2018.01); *G16H 10/60* (2018.01)

(58) Field of Classification Search
CPC ........ G16H 10/20; G16H 10/60; G06Q 10/10; G06Q 50/22; G06Q 50/24
See application file for complete search history.

(56) References Cited

U.S. PATENT DOCUMENTS

| | | |
|---|---|---|
| 5,172,419 A | 12/1992 | Manian |
| 5,179,651 A | 1/1993 | Taaffe et al. |
| 5,431,161 A | 7/1995 | Ryals et al. |
| 5,452,416 A | 9/1995 | Hilton et al. |
| 5,515,375 A | 5/1996 | DeClerck |
| 5,542,003 A | 7/1996 | Wofford |
| 5,734,915 A | 3/1998 | Roewer |
| 5,740,267 A | 4/1998 | Echerer et al. |
| 5,779,634 A | 7/1998 | Ema et al. |
| 5,807,256 A | 9/1998 | Taguchi |
| 5,835,030 A | 11/1998 | Tsutsui et al. |
| 5,852,646 A | 12/1998 | Klotz et al. |
| 5,857,030 A | 1/1999 | Gaborski |
| 5,926,568 A | 7/1999 | Chaney et al. |
| 5,954,650 A | 9/1999 | Saito et al. |
| 5,976,088 A | 11/1999 | Urbano et al. |
| 5,986,662 A | 11/1999 | Argiro et al. |
| 5,987,345 A | 11/1999 | Engelmann et al. |
| 5,995,644 A | 11/1999 | Lai et al. |
| 6,008,813 A | 12/1999 | Lauer et al. |
| 6,115,486 A | 9/2000 | Cantoni |
| 6,128,002 A | 10/2000 | Leiper |
| 6,130,671 A | 10/2000 | Agiro |
| 6,151,581 A | 11/2000 | Kraftson et al. |
| 6,175,643 B1 | 1/2001 | Lai et al. |
| 6,177,937 B1 | 1/2001 | Stockham et al. |
| 6,185,320 B1 | 2/2001 | Bick et al. |
| 6,211,795 B1 | 4/2001 | Izuta |
| 6,211,884 B1 | 4/2001 | Knittel et al. |
| 6,219,059 B1 | 4/2001 | Argiro |
| 6,219,061 B1 | 4/2001 | Lauer et al. |
| 6,243,095 B1 | 6/2001 | Shile et al. |
| 6,243,098 B1 | 6/2001 | Lauer et al. |
| 6,262,740 B1 | 7/2001 | Lauer et al. |
| 6,266,733 B1 | 7/2001 | Knittel et al. |
| 6,269,379 B1 | 7/2001 | Hiyama et al. |
| 6,297,799 B1 | 10/2001 | Knittel et al. |
| 6,304,667 B1 | 10/2001 | Reitano |
| 6,310,620 B1 | 10/2001 | Lauer et al. |
| 6,313,841 B1 | 11/2001 | Ogata et al. |
| 6,342,885 B1 | 1/2002 | Knittel et al. |
| 6,347,329 B1 | 2/2002 | Evans |
| 6,351,547 B1 | 2/2002 | Johnson et al. |
| 6,356,265 B1 | 3/2002 | Knittel et al. |
| 6,369,816 B1 | 4/2002 | Knittel et al. |
| 6,383,135 B1 | 5/2002 | Chikovani et al. |
| 6,388,687 B1 | 5/2002 | Brackett et al. |
| 6,404,429 B1 | 6/2002 | Knittel |
| 6,407,737 B1 | 6/2002 | Zhao et al. |
| 6,411,296 B1 | 6/2002 | Knittel et al. |
| 6,421,057 B1 | 7/2002 | Lauer et al. |
| 6,424,346 B1 | 7/2002 | Correll et al. |
| 6,424,996 B1 | 7/2002 | Killcommons et al. |
| 6,426,749 B1 | 7/2002 | Knittel et al. |
| 6,427,022 B1 | 7/2002 | Craine et al. |
| 6,438,533 B1 | 8/2002 | Spackman et al. |
| 6,463,169 B1 | 10/2002 | Ino et al. |
| 6,476,810 B1 | 11/2002 | Simha et al. |
| 6,512,517 B1 | 1/2003 | Knittel et al. |
| 6,532,299 B1 | 3/2003 | Sachdeva et al. |
| 6,532,311 B1 | 3/2003 | Pritt |
| 6,556,695 B1 | 4/2003 | Packer et al. |
| 6,556,724 B1 | 4/2003 | Chang et al. |
| 6,563,950 B1 | 5/2003 | Wiskott et al. |
| 6,574,629 B1 | 6/2003 | Cooke et al. |
| 6,577,753 B2 | 6/2003 | Ogawa |
| 6,603,494 B1 | 8/2003 | Banks et al. |
| 6,606,171 B1 | 8/2003 | Renk et al. |
| 6,614,447 B1 | 9/2003 | Bhatia et al. |
| 6,618,060 B1 | 9/2003 | Brackett |
| 6,621,918 B1 | 9/2003 | Hu et al. |
| 6,630,937 B2 | 10/2003 | Kallergi et al. |
| 6,650,766 B1 | 11/2003 | Rogers |
| 6,654,012 B1 | 11/2003 | Lauer et al. |
| 6,678,764 B2 | 1/2004 | Parvelescu et al. |
| 6,680,735 B1 | 1/2004 | Seiler et al. |
| 6,683,933 B2 | 1/2004 | Saito et al. |
| 6,697,067 B1 | 2/2004 | Callahan et al. |
| 6,697,506 B1 | 2/2004 | Oian et al. |
| 6,734,880 B2 | 5/2004 | Chang et al. |
| 6,760,755 B1 | 7/2004 | Brackett |
| 6,775,402 B2 | 8/2004 | Bacus et al. |
| 6,778,689 B1 | 8/2004 | Aksit et al. |
| 6,785,410 B2 | 8/2004 | Vining et al. |
| 6,820,093 B2 | 11/2004 | de la Huerga |
| 6,820,100 B2 | 11/2004 | Funahashi |
| 6,826,297 B2 | 11/2004 | Saito et al. |
| 6,829,377 B2 | 12/2004 | Milioto |
| 6,864,794 B2 | 3/2005 | Betz |
| 6,886,133 B2 | 4/2005 | Bailey et al. |
| 6,891,920 B1 | 5/2005 | Minyard et al. |
| 6,894,707 B2 | 5/2005 | Nemoto |
| 6,909,436 B1 | 6/2005 | Pianykh et al. |
| 6,909,795 B2 | 6/2005 | Tecotzky et al. |
| 6,917,696 B2 | 7/2005 | Soenksen |
| 6,988,075 B1 | 1/2006 | Hacker |
| 6,996,205 B2 | 2/2006 | Capolunghi et al. |
| 7,016,952 B2 | 3/2006 | Mullen et al. |
| 7,022,073 B2 | 4/2006 | Fan et al. |
| 7,027,633 B2 | 4/2006 | Foran et al. |
| 7,031,504 B1 | 4/2006 | Argiro et al. |
| 7,031,846 B2 | 4/2006 | Kaushikkar et al. |
| 7,039,723 B2 | 5/2006 | Hu et al. |
| 7,043,474 B2 | 5/2006 | Mojsilovic |
| 7,050,620 B2 | 5/2006 | Heckman |
| 7,054,473 B1 | 5/2006 | Roehrig et al. |
| 7,058,901 B1 | 6/2006 | Hafey et al. |
| 7,092,572 B2 | 8/2006 | Huang et al. |
| 7,103,205 B2 | 9/2006 | Wang et al. |
| 7,106,479 B2 | 9/2006 | Roy et al. |
| 7,110,616 B2 | 9/2006 | Ditt et al. |
| 7,113,186 B2 | 9/2006 | Kim et al. |
| 7,123,684 B2 | 10/2006 | Jing et al. |
| 7,136,064 B2 | 11/2006 | Zuiderveld |
| 7,139,416 B2 | 11/2006 | Vuylsteke |
| 7,149,334 B2 | 12/2006 | Dehmeshki |
| 7,155,043 B2 | 12/2006 | Daw |
| 7,162,623 B2 | 1/2007 | Yngvesson |
| 7,170,532 B2 | 1/2007 | Sako |
| 7,174,054 B2 | 2/2007 | Manber et al. |
| 7,209,149 B2 | 4/2007 | Jogo |
| 7,209,578 B2 | 4/2007 | Saito et al. |

(56) References Cited

U.S. PATENT DOCUMENTS

| | | |
|---|---|---|
| 7,212,661 B2 | 5/2007 | Samara et al. |
| 7,218,763 B2 | 5/2007 | Belykh et al. |
| 7,224,852 B2 | 5/2007 | Lipton et al. |
| 7,236,558 B2 | 6/2007 | Saito et al. |
| 7,260,249 B2 | 8/2007 | Smith |
| 7,263,710 B1 | 8/2007 | Hummel et al. |
| 7,272,610 B2 | 9/2007 | Torres |
| 7,346,199 B2 | 3/2008 | Pfaff |
| 7,366,992 B2 | 4/2008 | Thomas, III |
| 7,379,578 B2 | 5/2008 | Soussaline et al. |
| 7,412,111 B2 | 8/2008 | Battle et al. |
| 7,450,747 B2 | 11/2008 | Jabri et al. |
| 7,492,970 B2 | 2/2009 | Saito et al. |
| 7,505,782 B2 | 3/2009 | Chu |
| 7,516,417 B2 | 4/2009 | Amador et al. |
| 7,525,554 B2 | 4/2009 | Morita et al. |
| 7,526,114 B2 | 4/2009 | Seul et al. |
| 7,526,132 B2 | 4/2009 | Koenig |
| 7,545,965 B2 | 6/2009 | Suzuki et al. |
| 7,574,029 B2 | 8/2009 | Peterson et al. |
| 7,583,861 B2 | 9/2009 | Hanna et al. |
| 7,590,272 B2 | 9/2009 | Brejl et al. |
| 7,599,534 B2 | 10/2009 | Krishnan |
| 7,613,335 B2 | 11/2009 | McLennan et al. |
| 7,634,121 B2 | 12/2009 | Novatzky et al. |
| 7,636,413 B2 | 12/2009 | Toth |
| 7,639,879 B2 | 12/2009 | Goto et al. |
| 7,656,543 B2 | 2/2010 | Atkins |
| 7,660,481 B2 | 2/2010 | Schaap et al. |
| 7,660,488 B2 | 2/2010 | Reicher et al. |
| 7,668,352 B2 | 2/2010 | Tecotzky et al. |
| 7,683,909 B2 | 3/2010 | Takekoshi |
| 7,698,152 B2 | 4/2010 | Reid |
| 7,716,277 B2 | 5/2010 | Yamatake |
| 7,787,672 B2 | 8/2010 | Reicher et al. |
| 7,834,891 B2 | 11/2010 | Yarger et al. |
| 7,835,560 B2 | 11/2010 | Vining et al. |
| 7,885,440 B2 | 2/2011 | Fram et al. |
| 7,885,828 B2 | 2/2011 | Glaser-Seidnitzer et al. |
| 7,899,514 B1 | 3/2011 | Kirkland |
| 7,920,152 B2 | 4/2011 | Fram et al. |
| 7,941,462 B2 | 5/2011 | Akinyemi et al. |
| 7,953,614 B1 | 5/2011 | Reicher |
| 7,970,188 B2 | 6/2011 | Mahesh et al. |
| 7,970,625 B2 | 6/2011 | Reicher et al. |
| 7,991,210 B2 | 8/2011 | Peterson et al. |
| 8,019,138 B2 | 9/2011 | Reicher et al. |
| 8,046,044 B2 | 10/2011 | Stazzone et al. |
| 8,050,938 B1 | 11/2011 | Green, Jr. et al. |
| 8,065,166 B2 | 11/2011 | Maresh et al. |
| 8,073,225 B2 | 12/2011 | Hagen et al. |
| 8,094,901 B1 | 1/2012 | Reicher et al. |
| 8,150,708 B2 | 4/2012 | Kotula et al. |
| 8,214,756 B2 | 7/2012 | Salazar-Ferrer et al. |
| 8,217,966 B2 | 7/2012 | Fram et al. |
| 8,244,014 B2 | 8/2012 | Reicher et al. |
| 8,249,687 B2 | 8/2012 | Peterson et al. |
| 8,262,572 B2 | 9/2012 | Chono |
| 8,292,811 B2 | 10/2012 | Relkuntwar et al. |
| 8,298,147 B2 | 10/2012 | Huennekens et al. |
| 8,370,293 B2 | 2/2013 | Iwase et al. |
| 8,379,051 B2 | 2/2013 | Brown |
| 8,380,533 B2 | 2/2013 | Reicher et al. |
| 8,391,643 B2 | 3/2013 | Melbourne et al. |
| 8,406,491 B2 | 3/2013 | Gee et al. |
| 8,452,063 B2 | 5/2013 | Wojton et al. |
| 8,457,990 B1 | 6/2013 | Reicher et al. |
| 8,520,978 B2 | 8/2013 | Jakobovits |
| 8,554,576 B1 | 10/2013 | Reicher et al. |
| 8,560,050 B2 | 10/2013 | Martin et al. |
| 8,610,746 B2 | 12/2013 | Fram et al. |
| 8,626,527 B1 | 1/2014 | Reicher et al. |
| 8,693,757 B2 | 4/2014 | Gundel |
| 8,712,120 B1 | 4/2014 | Reicher et al. |
| 8,731,259 B2 | 5/2014 | Reicher et al. |
| 8,751,268 B1 | 6/2014 | Reicher et al. |
| 8,797,350 B2 | 8/2014 | Fram |
| 8,879,807 B2 | 11/2014 | Fram et al. |
| 8,913,808 B2 | 12/2014 | Reicher et al. |
| 8,954,884 B1 | 2/2015 | Barger |
| 8,976,190 B1 | 3/2015 | Westerhoff et al. |
| 9,042,617 B1 | 5/2015 | Reicher et al. |
| 9,075,899 B1 | 7/2015 | Reicher |
| 9,092,551 B1 | 7/2015 | Reicher |
| 9,092,727 B1 | 7/2015 | Reicher |
| 9,324,188 B1 | 4/2016 | Fram et al. |
| 9,386,084 B1 | 7/2016 | Reicher et al. |
| 9,471,210 B1 | 10/2016 | Fram et al. |
| 9,495,604 B1 | 11/2016 | Fram |
| 9,501,617 B1 | 11/2016 | Reicher et al. |
| 9,501,627 B2 | 11/2016 | Reicher et al. |
| 9,501,863 B1 | 11/2016 | Fram et al. |
| 9,542,082 B1 | 1/2017 | Reicher et al. |
| 9,672,477 B1 | 6/2017 | Reicher et al. |
| 9,684,762 B2 | 6/2017 | Reicher et al. |
| 9,727,938 B1 | 8/2017 | Reicher et al. |
| 9,734,576 B2 | 8/2017 | Fram et al. |
| 9,754,074 B1 | 9/2017 | Reicher et al. |
| 9,836,202 B1 | 12/2017 | Reicher et al. |
| 1,015,768 A1 | 12/2018 | Reicher et al. |
| 10,387,612 B2 | 8/2019 | Wu et al. |
| 2001/0016822 A1 | 8/2001 | Bessette |
| 2001/0042124 A1 | 11/2001 | Barron |
| 2002/0016718 A1 | 2/2002 | Rothschild et al. |
| 2002/0021828 A1 | 2/2002 | Papier et al. |
| 2002/0039084 A1 | 4/2002 | Yamaguchi |
| 2002/0044696 A1 | 4/2002 | Sirohey et al. |
| 2002/0070970 A1 | 6/2002 | Wood et al. |
| 2002/0073429 A1 | 6/2002 | Beane et al. |
| 2002/0090118 A1 | 7/2002 | Olschewski |
| 2002/0090119 A1 | 7/2002 | Saito et al. |
| 2002/0090124 A1 | 7/2002 | Soubelet et al. |
| 2002/0091659 A1 | 7/2002 | Beaulieu et al. |
| 2002/0103673 A1 | 8/2002 | Atwood |
| 2002/0103827 A1 | 8/2002 | Sesek |
| 2002/0106119 A1 | 8/2002 | Foran et al. |
| 2002/0110285 A1 | 8/2002 | Wang et al. |
| 2002/0144697 A1 | 10/2002 | Betz |
| 2002/0145941 A1 | 10/2002 | Poland et al. |
| 2002/0172408 A1 | 11/2002 | Saito et al. |
| 2002/0172409 A1 | 11/2002 | Saito et al. |
| 2002/0180883 A1 | 12/2002 | Tomizawa et al. |
| 2002/0186820 A1 | 12/2002 | Saito et al. |
| 2002/0188637 A1 | 12/2002 | Bailey et al. |
| 2002/0190984 A1 | 12/2002 | Seiler et al. |
| 2003/0005464 A1 | 1/2003 | Gropper et al. |
| 2003/0013951 A1 | 1/2003 | Stefanescu |
| 2003/0016850 A1 | 1/2003 | Kaufman et al. |
| 2003/0028402 A1 | 2/2003 | Ulrich et al. |
| 2003/0034973 A1 | 2/2003 | Zuiderveld |
| 2003/0037054 A1 | 2/2003 | Dutta et al. |
| 2003/0053668 A1 | 3/2003 | Ditt et al. |
| 2003/0055896 A1 | 3/2003 | Hu et al. |
| 2003/0065613 A1 | 4/2003 | Smith |
| 2003/0071829 A1 | 4/2003 | Bodicker et al. |
| 2003/0101291 A1 | 5/2003 | Mussack et al. |
| 2003/0115083 A1 | 6/2003 | Masarie et al. |
| 2003/0120516 A1 | 6/2003 | Perednia |
| 2003/0130973 A1 | 7/2003 | Sumner, II et al. |
| 2003/0140044 A1 | 7/2003 | Mok et al. |
| 2003/0140141 A1 | 7/2003 | Mullen et al. |
| 2003/0156745 A1 | 8/2003 | Saito et al. |
| 2003/0160095 A1 | 8/2003 | Segal |
| 2003/0164860 A1 | 9/2003 | Shen et al. |
| 2003/0184778 A1 | 10/2003 | Chiba |
| 2003/0187689 A1 | 10/2003 | Barnes et al. |
| 2003/0190062 A1 | 10/2003 | Noro et al. |
| 2003/0195416 A1 | 10/2003 | Toth |
| 2003/0204420 A1 | 10/2003 | Wilkes et al. |
| 2003/0215120 A1 | 11/2003 | Uppaluri et al. |
| 2003/0215122 A1 | 11/2003 | Tanaka |
| 2004/0008900 A1 | 1/2004 | Jabri et al. |
| 2004/0015703 A1 | 1/2004 | Madison et al. |
| 2004/0024303 A1 | 2/2004 | Banks et al. |

(56) References Cited

U.S. PATENT DOCUMENTS

| | | |
|---|---|---|
| 2004/0027359 A1 | 2/2004 | Aharon et al. |
| 2004/0061889 A1 | 4/2004 | Wood et al. |
| 2004/0068170 A1 | 4/2004 | Wang et al. |
| 2004/0077952 A1 | 4/2004 | Rafter et al. |
| 2004/0086163 A1 | 5/2004 | Moriyama et al. |
| 2004/0088192 A1 | 5/2004 | Schmidt et al. |
| 2004/0105030 A1 | 6/2004 | Yamane |
| 2004/0105574 A1 | 6/2004 | Pfaff |
| 2004/0114714 A1 | 6/2004 | Minyard et al. |
| 2004/0122705 A1 | 6/2004 | Sabol et al. |
| 2004/0122787 A1 | 6/2004 | Avinash et al. |
| 2004/0141661 A1 | 7/2004 | Hanna et al. |
| 2004/0143582 A1 | 7/2004 | Vu |
| 2004/0161139 A1 | 8/2004 | Samara et al. |
| 2004/0161164 A1 | 8/2004 | Dewaele |
| 2004/0165791 A1 | 8/2004 | Kaltanji |
| 2004/0172306 A1 | 9/2004 | Wohl et al. |
| 2004/0174429 A1 | 9/2004 | Chu |
| 2004/0190780 A1 | 9/2004 | Shiibashi et al. |
| 2004/0197015 A1 | 10/2004 | Fan et al. |
| 2004/0202387 A1 | 10/2004 | Yngvesson |
| 2004/0243435 A1 | 12/2004 | Williams |
| 2004/0252871 A1 | 12/2004 | Tecotzky et al. |
| 2004/0254816 A1 | 12/2004 | Myers |
| 2004/0255252 A1 | 12/2004 | Rodriguez et al. |
| 2005/0010531 A1 | 1/2005 | Kushalnagar et al. |
| 2005/0027569 A1 | 2/2005 | Gollogly et al. |
| 2005/0027570 A1 | 2/2005 | Maier et al. |
| 2005/0043970 A1 | 2/2005 | Hsieh |
| 2005/0063575 A1 | 3/2005 | Ma et al. |
| 2005/0065424 A1 | 3/2005 | Shah et al. |
| 2005/0074150 A1 | 4/2005 | Bruss |
| 2005/0074157 A1 | 4/2005 | Thomas, III |
| 2005/0075544 A1 | 4/2005 | Shapiro et al. |
| 2005/0088534 A1 | 4/2005 | Shen et al. |
| 2005/0107689 A1 | 5/2005 | Sasano |
| 2005/0108058 A1 | 5/2005 | Weidner et al. |
| 2005/0110791 A1 | 5/2005 | Krishnamoorthy et al. |
| 2005/0111733 A1 | 5/2005 | Fors et al. |
| 2005/0113681 A1 | 5/2005 | DeFreitas et al. |
| 2005/0114178 A1 | 5/2005 | Krishnamurthy et al. |
| 2005/0114179 A1 | 5/2005 | Brackett et al. |
| 2005/0114283 A1 | 5/2005 | Pearson et al. |
| 2005/0143654 A1 | 6/2005 | Zuiderveld et al. |
| 2005/0171818 A1 | 8/2005 | McLaughlin |
| 2005/0184988 A1 | 8/2005 | Yanof et al. |
| 2005/0197860 A1 | 9/2005 | Joffe et al. |
| 2005/0238218 A1 | 10/2005 | Nakamura |
| 2005/0244041 A1 | 11/2005 | Tecotzky et al. |
| 2005/0251013 A1 | 11/2005 | Krishnan |
| 2005/0254729 A1 | 11/2005 | Saito et al. |
| 2005/0273009 A1 | 12/2005 | Deischinger et al. |
| 2006/0008181 A1 | 1/2006 | Takekoshi |
| 2006/0031097 A1 | 2/2006 | Lipscher et al. |
| 2006/0050152 A1 | 3/2006 | Rai et al. |
| 2006/0058603 A1 | 3/2006 | Dave et al. |
| 2006/0061570 A1 | 3/2006 | Cheryauka et al. |
| 2006/0093198 A1 | 5/2006 | Fram et al. |
| 2006/0093199 A1 | 5/2006 | Fram et al. |
| 2006/0093207 A1 | 5/2006 | Reicher et al. |
| 2006/0095423 A1 | 5/2006 | Reicher et al. |
| 2006/0095426 A1 | 5/2006 | Takachio et al. |
| 2006/0106642 A1 | 5/2006 | Reicher et al. |
| 2006/0111941 A1 | 5/2006 | Blom |
| 2006/0122482 A1 | 6/2006 | Mariotti et al. |
| 2006/0171574 A1 | 8/2006 | DelMonego et al. |
| 2006/0181548 A1 | 8/2006 | Hafey |
| 2006/0188134 A1 | 8/2006 | Quist |
| 2006/0230072 A1 | 10/2006 | Partovi et al. |
| 2006/0239573 A1 | 10/2006 | Novatzky et al. |
| 2006/0241979 A1 | 10/2006 | Sato et al. |
| 2006/0267976 A1 | 11/2006 | Saito et al. |
| 2006/0276708 A1 | 12/2006 | Peterson et al. |
| 2006/0277075 A1 | 12/2006 | Salwan |
| 2006/0282408 A1 | 12/2006 | Wisely et al. |
| 2007/0009078 A1 | 1/2007 | Saito et al. |
| 2007/0021977 A1 | 1/2007 | Elsholz |
| 2007/0050701 A1 | 3/2007 | El Emam et al. |
| 2007/0055550 A1 | 3/2007 | Courtney et al. |
| 2007/0064984 A1 | 3/2007 | Vassa et al. |
| 2007/0067124 A1 | 3/2007 | Kimpe et al. |
| 2007/0073556 A1 | 3/2007 | Lau et al. |
| 2007/0106535 A1 | 5/2007 | Matsunaga |
| 2007/0106633 A1 | 5/2007 | Reiner |
| 2007/0109299 A1 | 5/2007 | Peterson |
| 2007/0109402 A1 | 5/2007 | Niwa |
| 2007/0110294 A1 | 5/2007 | Schaap et al. |
| 2007/0116345 A1 | 5/2007 | Peterson et al. |
| 2007/0116346 A1 | 5/2007 | Peterson et al. |
| 2007/0122016 A1 | 5/2007 | Brejl et al. |
| 2007/0124541 A1 | 5/2007 | Lang et al. |
| 2007/0140536 A1 | 6/2007 | Sehnert |
| 2007/0159962 A1 | 7/2007 | Mathavu et al. |
| 2007/0162308 A1 | 7/2007 | Peters |
| 2007/0165917 A1 | 7/2007 | Cao et al. |
| 2007/0174079 A1 | 7/2007 | Kraus |
| 2007/0192138 A1 | 8/2007 | Saito et al. |
| 2007/0192140 A1 | 8/2007 | Gropper |
| 2007/0237380 A1 | 10/2007 | Iwase et al. |
| 2007/0239481 A1 | 10/2007 | DiSilvestro et al. |
| 2007/0245308 A1* | 10/2007 | Hill ............... G06F 17/2247 717/114 |
| 2008/0016111 A1 | 1/2008 | Keen |
| 2008/0019581 A1 | 1/2008 | Gkanatsios et al. |
| 2008/0021877 A1 | 1/2008 | Saito et al. |
| 2008/0031507 A1 | 2/2008 | Uppaluri et al. |
| 2008/0059245 A1 | 3/2008 | Sakaida et al. |
| 2008/0097186 A1 | 4/2008 | Biglieri et al. |
| 2008/0100612 A1 | 5/2008 | Dastmalchi et al. |
| 2008/0103828 A1 | 5/2008 | Squilla et al. |
| 2008/0118120 A1 | 5/2008 | Wegenkittl et al. |
| 2008/0125846 A1 | 5/2008 | Battle et al. |
| 2008/0126982 A1 | 5/2008 | Sadikali et al. |
| 2008/0133526 A1 | 6/2008 | Haitani et al. |
| 2008/0136838 A1 | 6/2008 | Goede et al. |
| 2008/0275913 A1 | 11/2008 | van Arragon et al. |
| 2008/0279439 A1 | 11/2008 | Minyard et al. |
| 2008/0300484 A1 | 12/2008 | Wang et al. |
| 2009/0005668 A1 | 1/2009 | West et al. |
| 2009/0022375 A1 | 1/2009 | Fidrich |
| 2009/0028410 A1 | 1/2009 | Shimazaki |
| 2009/0080719 A1 | 3/2009 | Watt |
| 2009/0091566 A1 | 4/2009 | Turney et al. |
| 2009/0123052 A1 | 5/2009 | Ruth et al. |
| 2009/0129643 A1 | 5/2009 | Natanzon et al. |
| 2009/0129651 A1 | 5/2009 | Zagzebski et al. |
| 2009/0132586 A1* | 5/2009 | Napora ............... G16H 40/20 |
| 2009/0150811 A1 | 6/2009 | Garcia et al. |
| 2009/0164247 A1 | 6/2009 | Dobler et al. |
| 2009/0182577 A1 | 7/2009 | Squilla et al. |
| 2009/0198514 A1* | 8/2009 | Rhodes ............... G06Q 50/22 705/3 |
| 2009/0213034 A1 | 8/2009 | Wu et al. |
| 2009/0248442 A1 | 10/2009 | Pacheco et al. |
| 2009/0268986 A1 | 10/2009 | Holstein et al. |
| 2009/0326373 A1 | 12/2009 | Boese et al. |
| 2010/0053353 A1 | 3/2010 | Hunter et al. |
| 2010/0086182 A1 | 4/2010 | Hui |
| 2010/0131887 A1 | 5/2010 | Salazar-Ferrer et al. |
| 2010/0138239 A1 | 6/2010 | Reicher et al. |
| 2010/0198608 A1 | 8/2010 | Kaboff et al. |
| 2010/0201714 A1 | 8/2010 | Reicher et al. |
| 2010/0211409 A1 | 8/2010 | Kotula et al. |
| 2010/0246981 A1 | 9/2010 | Hu et al. |
| 2010/0299157 A1 | 11/2010 | Fram et al. |
| 2011/0016430 A1 | 1/2011 | Fram et al. |
| 2011/0019886 A1 | 1/2011 | Mizuno |
| 2011/0110572 A1 | 5/2011 | Guehring et al. |
| 2011/0267339 A1 | 11/2011 | Fram et al. |
| 2011/0293162 A1 | 12/2011 | Pajeau |
| 2011/0316873 A1 | 12/2011 | Reicher et al. |
| 2012/0070048 A1 | 3/2012 | Van Den Brink |
| 2012/0130729 A1 | 5/2012 | Raizada et al. |
| 2012/0136794 A1 | 5/2012 | Kushalnagar et al. |

(56) References Cited

U.S. PATENT DOCUMENTS

| | | |
|---|---|---|
| 2012/0163684 A1 | 6/2012 | Natanzon et al. |
| 2012/0183191 A1 | 7/2012 | Nakamura |
| 2012/0194540 A1 | 8/2012 | Reicher et al. |
| 2012/0196258 A1 | 8/2012 | Geijsen et al. |
| 2012/0284657 A1 | 11/2012 | Hafey et al. |
| 2012/0320093 A1 | 12/2012 | Zhu et al. |
| 2012/0324400 A1 | 12/2012 | Caliendo, Jr. et al. |
| 2013/0070998 A1 | 3/2013 | Shibata |
| 2013/0076681 A1 | 3/2013 | Sirpal et al. |
| 2013/0083023 A1 | 4/2013 | Fram et al. |
| 2013/0129198 A1 | 5/2013 | Sherman et al. |
| 2013/0129231 A1 | 5/2013 | Dale et al. |
| 2013/0159019 A1 | 6/2013 | Reicher et al. |
| 2013/0169661 A1 | 7/2013 | Reicher et al. |
| 2013/0195329 A1 | 8/2013 | Canda et al. |
| 2013/0198682 A1 | 8/2013 | Matas et al. |
| 2013/0297331 A1 | 11/2013 | Zuehlsdorff et al. |
| 2014/0022194 A1 | 1/2014 | Ito |
| 2014/0096049 A1 | 4/2014 | Vonshak et al. |
| 2014/0119514 A1 | 5/2014 | Miyazawa |
| 2014/0142983 A1 | 5/2014 | Backhaus et al. |
| 2014/0378810 A1 | 12/2014 | Davis et al. |
| 2015/0046349 A1 | 2/2015 | Michael, Jr. et al. |
| 2015/0101066 A1 | 4/2015 | Fram |
| 2015/0363104 A1 | 12/2015 | Ichioka et al. |
| 2016/0034110 A1 | 2/2016 | Edwards |
| 2016/0270746 A1 | 9/2016 | Foos et al. |
| 2017/0038951 A1 | 2/2017 | Reicher et al. |
| 2017/0039321 A1 | 2/2017 | Reicher et al. |
| 2017/0039322 A1 | 2/2017 | Reicher et al. |
| 2017/0039705 A1 | 2/2017 | Fram et al. |
| 2017/0046014 A1 | 2/2017 | Fram |
| 2017/0046483 A1 | 2/2017 | Reicher et al. |
| 2017/0046485 A1 | 2/2017 | Reicher et al. |
| 2017/0046495 A1 | 2/2017 | Fram |
| 2017/0046870 A1 | 2/2017 | Fram et al. |
| 2017/0053404 A1 | 2/2017 | Reicher et al. |

OTHER PUBLICATIONS

US 8,208,705 B2, 06/2012, Reicher et al. (withdrawn)
U.S. Appl. No. 14/540,830, Systems and Methods for Viewing Medical Images, filed Nov. 13, 2014.
U.S. Appl. No. 15/254,627, Systems and Methods for Interleaving Series of Medical Images, filed Sep. 1, 2016.
U.S. Appl. No. 14/095,123, Systems and Methods for Retrieval of Medical Data, filed Dec. 3, 2013.
U.S. Appl. No. 14/081,225, Systems and Methods for Viewing Medical 3D Imaging Volumes, filed Nov. 15, 2013.
U.S. Appl. No. 14/244,431, Systems and Methods for Matching, Naming, and Displaying Medical Images, filed Apr. 3, 2014.
U.S. Appl. No. 14/298,806, Smart Placement Rules, filed Jun. 6, 2013.
U.S. Appl. No. 11/942,687, Smart Forms, filed Nov. 19, 2007.
U.S. Appl. No. 14/043,165, Automated Document Filings, filed Oct. 1, 2013.
U.S. Appl. No. 11/944,000, Exam Scheduling With Customer Configured Notifications, filed Nov. 21, 2007.
U.S. Appl. No. 15/163,600, Rules-Based Approach to Transferring and/or Viewing Medical Images, filed May 24, 2016.
U.S. Appl. No. 14/792,210, Dynamic Montage Reconstruction, filed Jul. 6, 2015.
U.S. Appl. No. 15/140,346, Database Systems and Interactive User Interfaces for Dynamic Interaction With, and Sorting of, Digital Medical Image Data, filed Apr. 27, 2016.
U.S. Appl. No. 15/140,363, Database Systems and Interactive User Interfaces for Dynamic Interation With, and Comparison of, Digital Medical Image Data, filed Apr. 27, 2016.
U.S. Appl. No. 15/140,351, Database Systems and Interactive User Interfaces for Dynamic Interaction With, and Review of, Digital Medical Image DA, filed Apr. 27, 2016.
U.S. Appl. No. 15/140,348, Database Systems and Interactive User Interfaces for Dynamic Interaction With, and Indications of, Digital Medical Image Data, filed Apr. 27, 2016.
Non-Final Office Action dated Aug. 28, 2007 in U.S. Appl. No. 11/179,384.
Final Office Action dated Jun. 26, 2008 in U.S. Appl. No. 11/179,384.
Non-Final Office Action dated Dec. 29, 2008 in U.S. Appl. No. 11/179,384.
Final Office Action dated Jul. 24, 2009, in U.S. Appl. No. 11/179,384.
Notice of Allowance dated Nov. 3, 2009, in U.S. Appl. No. 11/179,384.
Non-Final Office Action dated Aug. 18, 2010 in U.S. Appl. No. 12/702,976.
Interview Summary dated Dec. 1, 2010, in U.S. Appl. No. 12/702,976.
Final Office Action dated Feb. 17, 2011 in U.S. Appl. No. 12/702,976.
Interview Summary dated May 31, 2011 in U.S. Appl. No. 12/702,976.
Notice of Allowance dated Jul. 20, 2011, in U.S. Appl. No. 12/702,976.
Office Action dated Dec. 1, 2011, in U.S. Appl. No. 13/228,349.
Notice of Allowance dated Feb. 6, 2012, in U.S. Appl. No. 13/228,349.
Notice of Allowance dated Jul. 20, 2012, in U.S. Appl. No. 13/228,349.
Office Action dated Dec. 11, 2013, in U.S. Appl. No. 13/477,853.
Interview Summary dated Mar. 14, 2014, in U.S. Appl. No. 13/477,853.
Final Office Action dated Jun. 13, 2014, in U.S. Appl. No. 13/477,853.
Notice of Allowance dated Aug. 15, 2014, in U.S. Appl. No. 13/477,853.
Non-Final Office Action dated Oct. 1, 2009, in U.S. Appl. No. 11/268,261.
Notice of Allowance dated Feb. 2, 2010, in U.S. Appl. No. 11/268,261.
Interview Summary dated Jan. 25, 2010, in U.S. Appl. No. 11/268,261.
Interview Summary dated May 14, 2010, in U.S. Appl. No. 11/268,261.
Notice of Allowance dated May 17, 2010, in U.S. Appl. No. 11/268,261.
Supplemental Notice of Allowance dated Aug. 6, 2010, in U.S. Appl. No. 11/268,261.
Notice of Allowance dated Oct. 8, 2010, in U.S. Appl. No. 11/268,261.
Notice of Allowance dated Dec. 3, 2010, in U.S. Appl. No. 11/268,261.
Notice of Allowance dated Jan. 6, 2011, in U.S. Appl. No. 11/268,261.
Office Action dated May 16, 2011, in U.S. Appl. No. 12/857,915.
Interview Summary dated Sep. 6, 2011, in U.S. Appl. No. 12/857,915.
Final Office Action dated Dec. 15, 2011, in U.S. Appl. No. 12/857,915.
Office Action dated Jun. 12, 2012, in U.S. Appl. No. 12/857,915.
Office Action dated Aug. 23, 2013, in U.S. Appl. No. 12/857,915.
Interview Summary dated Feb. 4, 2014, in U.S. Appl. No. 12/857,915.
Notice of Allowance dated Jul. 3, 2014, in U.S. Appl. No. 12/857,915.
"Corrected" Notice of Allowance dated Aug. 15, 2014, in U.S. Appl. No. 12/857,915.
Non-Final Office Action dated Jan. 20, 2016, in U.S. Appl. No. 14/502,055.
Interview Summary dated Apr. 14, 2016, in U.S. Appl. No. 14/502,055.
Notice of Allowance dated Jun. 2, 2016, in U.S. Appl. No. 14/502,055.
Notice of Corrected Allowability dated Jul. 14, 2016, in U.S. Appl. No. 14/502,055.
Notice of Corrected Allowability dated Sep. 19, 2016, in U.S. Appl. No. 14/502,055.
Non-Final Office Action dated May 13, 2009, in U.S. Appl. No. 11/265,979.
Final Office Action dated Dec. 22, 2009 in U.S. Appl. No. 11/265,979.
Non-Final Office Action dated Jul. 8, 2010 in U.S. Appl. No. 11/265,979.
Interview Summary dated Mar. 4, 2010 in U.S. Appl. No. 11/265,979.
Interview Summary dated Nov. 16, 2010 in U.S. Appl. No. 11/265,979.
Final Office Action dated Dec. 23, 2010 in U.S. Appl. No. 11/265,979.
Interview Summary dated Mar. 17, 2011 in U.S. Appl. No. 11/265,979.
Notice of Allowance dated May 26, 2011 in U.S. Appl. No. 11/265,979.
Office Action dated Jun. 8, 2012 in U.S. Appl. No. 13/171,081.
Interview Summary dated Jul. 31, 2012 in U.S. Appl. No. 13/171,081.
Final Office Action dated Oct. 12, 2012 in U.S. Appl. No. 13/171,081.
Interview Summary dated Nov. 6, 2012 in U.S. Appl. No. 13/171,081.

(56) References Cited

OTHER PUBLICATIONS

Notice of Allowance, dated Sep. 4, 2013, in U.S. Appl. No. 13/171,081.
Office Action dated Mar. 3, 2015 in U.S. Appl. No. 14/095,123.
Interview Summary dated May 1, 2015 in U.S. Appl. No. 14/095,123.
Final Office Action dated Jul. 23, 2015 in U.S. Appl. No. 14/095,123.
Interview Summary dated Aug. 27, 2015 in U.S. Appl. No. 14/095,123.
Office Action dated Feb. 23, 2016 in U.S. Appl. No. 14/095,123.
Final Office Action dated Jul. 20, 2016 in U.S. Appl. No. 14/095,123.
Non-Final Office Action dated Aug. 24, 2009 in U.S. Appl. No. 11/268,262.
Non-Final Office Action dated Apr. 16, 2010 in U.S. Appl. No. 11/268,262.
Interview Summary dated Nov. 24, 2009 in U.S. Appl. No. 11/268,262.
Interview Summary dated May 12, 2010 in U.S. Appl. No. 11/268,262.
Final Office Action dated Oct. 28, 2010 in U.S. Appl. No. 11/268,262.
Interview Summary dated Dec. 1, 2010 in U.S. Appl. No. 11/268,262.
Notice of Allowance dated Dec. 1, 2010 in U.S. Appl. No. 11/268,262.
Notice of Allowance dated Feb. 25, 2011 in U.S. Appl. No. 11/268,262.
Non-Final Office Action dated Jan. 11, 2012 in U.S. Appl. No. 13/079,597.
Notice of Allowance dated Apr. 25, 2012, in U.S. Appl. No. 13/079,597.
Non-Final Office Action dated Apr. 4, 2013 in U.S. Appl. No. 13/535,758.
Notice of Allowance, dated Aug. 23, 2013 in U.S. Appl. No. 13/535,758.
Corrected Notice of Allowance dated Jun. 27, 2016, in U.S. Appl. No. 14/502,055.
Office Action dated Mar. 10, 2016 in U.S. Appl. No. 14/081,225.
Notice of Allowance dated Sep. 2, 2016 in U.S. Appl. No. 14/081,225.
Non-Final Office Action dated Jul. 27, 2009 in U.S. Appl. No. 11/265,978.
Notice of Allowance dated Nov. 19, 2009 in U.S. Appl. No. 11/265,978.
Notice of Allowance dated Apr. 19, 2010 in U.S. Appl. No. 11/265,978.
Supplemental Notice of Allowance dated May 3, 2010 in U.S. Appl. No. 11/265,978.
Supplemental Notice of Allowance dated Aug. 3, 2010 in U.S. Appl. No. 11/265,978.
Non-Final Office Action dated May 5, 2011 in U.S. Appl. No. 12/870,645.
Non-Final Office Action dated May 31, 2013, in U.S. Appl. No. 13/345,606.
Interview Summary dated Aug. 15, 2013, in U.S. Appl. No. 13/345,606.
Notice of Allowance, dated Jan. 9, 2014 in U.S. Appl. No. 13/345,606.
Non-Final Office Action dated Mar. 18, 2016 in U.S. Appl. No. 14/244,431.
Interview Summary dated Jun. 17, 2016 in U.S. Appl. No. 14/244,431.
Notice of Allowance dated Aug. 18, 2016 in U.S. Appl. No. 14/244,431.
Non-Final Office Action dated May 26, 2010 in U.S. Appl. No. 11/942,674.
Interview Summary dated Jul. 26, 2010 in U.S. Appl. No. 11/942,674.
Final Office Action dated Nov. 26, 2010 in U.S. Appl. No. 11/942,674.
Interview Summary dated Mar. 2, 2011 in U.S. Appl. No. 11/942,674.
Notice of Allowance, dated Apr. 1, 2011 in U.S. Appl. No. 11/942,674.
Non Final Office Action dated Nov. 10, 2011 in U.S. Appl. No. 13/118,085.
Interview Summary, dated Feb. 17, 2012, in U.S. Appl. No. 13/118,085.
Final Office Action, dated Apr. 13, 2012, in U.S. Appl. No. 13/118,085.
Notice of Allowance, dated Feb. 6, 2013, in U.S. Appl. No. 13/118,085.
Non Final Office Action dated Aug. 23, 2013 in U.S. Appl. No. 13/907,128.
Final Office Action dated Oct. 9, 2013 in U.S. Appl. No. 13/907,128.
Interview Summary dated Nov. 22, 2013 in U.S. Appl. No. 13/907,128.
Notice of Allowance dated Jan. 31, 2014 in U.S. Appl. No. 13/907,128.
Office Action, dated Dec. 29, 2014 in U.S. Appl. No. 14/298,806.
Interview Summary, dated Mar. 2, 2015 in U.S. Appl. No. 14/298,806.
Final Office Action, dated Jun. 17, 2015 in U.S. Appl. No. 14/298,806.
Office Action, dated Feb. 16, 2016 in U.S. Appl. No. 14/298,806.
Final Office Action, dated Jul. 21, 2016 in U.S. Appl. No. 14/298,806.
Non Final Office Action dated Sep. 16, 2010 in U.S. Appl. No. 11/942,687.
Interview Summary dated Dec. 3, 2010 in U.S. Appl. No. 11/942,687.
Final Office Action, dated Apr. 5, 2011 in U.S. Appl. No. 11/942,687.
Office Action, dated Mar. 13, 2014 in U.S. Appl. No. 11/942,687.
Interview Summary, dated Jun. 17, 2014 in U.S. Appl. No. 11/942,687.
Office Action, dated Jul. 18, 2014 in U.S. Appl. No. 11/942,687.
Final Office Action, dated Jan. 5, 2015 in U.S. Appl. No. 11/942,687.
Interview Summary, dated Mar. 4, 2015 in U.S. Appl. No. 11/942,687.
Ptab Examiner's Answer, dated Feb. 25, 2016 in U.S. Appl. No. 11/942,687.
Non-Final Office Action dated Apr. 14, 2010 in U.S. Appl. No. 11/944,027.
Interview Summary dated May 13, 2010 in U.S. Appl. No. 11/944,027.
Final Office Action dated Dec. 23, 2010 in U.S. Appl. No. 11/944,027.
Interview Summary dated Mar. 31, 2011 in U.S. Appl. No. 11/944,027.
Office Action dated Apr. 19, 2012 in U.S. Appl. No. 11/944,027.
Interview Summary dated Jun. 28, 2012 in U.S. Appl. No. 11/944,027.
Final Office Action dated Oct. 22, 2012 in U.S. Appl. No. 11/944,027.
Notice of Allowance dated Jun. 5, 2013 in U.S. Appl. No. 11/944,027.
Office Action dated Oct. 14, 2014 in U.S. Appl. No. 14/043,165.
Final Office Action dated Apr. 1, 2015 in U.S. Appl. No. 14/043,165.
Office Action dated Oct. 2, 2015 in U.S. Appl. No. 14/043,165.
Interview Summary dated Dec. 21, 2015 in U.S. Appl. No. 14/043,165.
Final Office Action dated Feb. 17, 2016 in U.S. Appl. No. 14/043,165.
Non-Final Office Action dated Sep. 29, 2010 in U.S. Appl. No. 11/944,000.
Final Office Action dated Apr. 20, 2011 in U.S. Appl. No. 11/944,000.
Interview Summary dated Jun. 7, 2011 in U.S. Appl. No. 11/944,000.
Appeal Brief dated Mar. 4, 2013 in U.S. Appl. No. 11/944,000.
Examiner's Answer dated Jun. 26, 2013 in U.S. Appl. No. 11/944,000.
Board Decision dated Mar. 23, 2016 in U.S. Appl. No. 11/944,000.
Office Action, dated Jul. 15, 2016 in U.S. Appl. No. 11/944,000.
Office Action dated Feb. 3, 2012 in U.S. Appl. No. 12/622,404.
Interview Summary dated May 8, 2012 in U.S. Appl. No. 12/622,404.
Final Office Action dated Aug. 6, 2012 in U.S. Appl. No. 12/622,404.
Notice of Allowance dated Oct. 15, 2012 in U.S. Appl. No. 12/622,404.
Notice of Allowance dated Aug. 28, 2015 in U.S. Appl. No. 13/768,765.
Notice of Allowability dated Nov. 20, 2015 in U.S. Appl. No. 13/768,765.
Notice of Allowability dated Jul. 28, 2016 in U.S. Appl. No. 13/768,765.
Office Action dated Mar. 4, 2013 in U.S. Appl. No. 12/891,543.
Interview Summary dated Apr. 5, 2013 in U.S. Appl. No. 12/891,543.
Notice of Allowance dated Nov. 14, 2013 in U.S. Appl. No. 12/891,543.
Office Action dated Sep. 11, 2014 in U.S. Appl. No. 14/179,328.
Notice of Allowance dated Jan. 14, 2015 in U.S. Appl. No. 14/179,328.
Office Action dated Aug. 13, 2015 in U.S. Appl. No. 14/687,853.
Notice of Allowance dated Feb. 25, 2016 in U.S. Appl. No. 14/687,853.
Supplemental Notice of Allowance dated Jun. 2, 2016 in U.S. Appl. No. 14/687,853.
Notice of Allowance dated Aug. 11, 2016 in U.S. Appl. No. 15/163,600.
Supplemental Notice of Allowance dated Sep. 14, 2016 in U.S. Appl. No. 15/163,600.
Office Action dated Jun. 27, 2014 in U.S. Appl. No. 13/572,397.
Final Office Action dated Jan. 13, 2015 in U.S. Appl. No. 13/572,397.
Notice of Allowance dated Mar. 19, 2015, 2015 in U.S. Appl. No. 13/572,397.
Office Action dated Aug. 6, 2014 in U.S. Appl. No. 13/572,547.
Notice of Allowance, dated Mar. 3, 2015 in U.S. Appl. No. 13/572,547.

(56) References Cited

OTHER PUBLICATIONS

Corrected Notice of Allowance, dated Apr. 10, 2015 in U.S. Appl. No. 13/572,547.
Corrected Notice of Allowance, dated May 21, 2015 in U.S. Appl. No. 13/572,547.
Office Action dated Jul. 30, 2014 in U.S. Appl. No. 13/572,552.
Interview Summary dated Sep. 3, 2014 in U.S. Appl. No. 13/572,552.
Final Office Action dated Jan. 28, 2015 in U.S. Appl. No. 13/572,552.
Interview Summary dated Apr. 23, 2015 in U.S. Appl. No. 13/572,552.
Notice of Allowance, dated May 8, 2015 in U.S. Appl. No. 13/572,552.
AGFA HealthCare, color brochure "IMPAX 6: Digital Image and Information Management," ©2012 Agfa HealthCare N.V. Downloaded from http://www.agfahealthcare.com/global/en/he/library/libraryopen?ID=32882925. Accessed on Feb. 9, 2015.
AGFA HealthCare, IMPAX 6.5 Datasheet (US)2012. ©2012 Agfa HealthCare N.V. Downloaded from http://www.agfahealthcare.com/global/en/he/library/libraryopen?ID=37459801. Accessed on Feb. 9, 2015.
AMD Technologies, Inc., Catella PACS 5.0 Viewer User Manual (112 pgs), © 2010, AMD Technologies, Inc. (Doc. 340-3-503 Rev. 01). Downloaded from http://www.amdtechnologies.com/lit/cat5viewer.pdf. Accessed on Feb. 9, 2015.
ASYRA's Imaging Solutions, 3 page color print out. Accessed at http://www.aspyra.com/imaging-solutions. Accessed on Feb. 9, 2015.
AVREO, interWorks—RIS/PACS package, 2 page color brochure, © 2014, Avreo, Inc. (Document MR-5032 Rev. 4). Downloaded from http://www.avreo.com/ProductBrochures/MR-5032Rev.%204interWORKS%20RISPACSPackage.pdf. Accessed on Feb. 9, 2015.
BRIT Systems, BRIT PACS View Viewer, 2 pages color brochure, (BPB-BPV-0001). Downloaded from http://www.brit.com/pdfs/britpacsview.pdf. Accessed on Feb. 9, 2015.
BRIT Systems, Roentgen Works—100% Browers-based VNA (Vendor Neutral Archive/PACS), © 2010 BRIT Systems, 1 page color sheet. Accessed at http://www.roentgenworks.com/PACS. Accessed on Feb. 9, 2015.
BRIT Systems, Vision Multi-modality Viewer—with 3D, 2 page color brochure, (BPB-BVV-0001 REVC). Downloaded from http://www.brit.com/pdfs/BPB-BVV-0001REVC_BRIT_Vision_Viewer.pdf. Accessed on Feb. 9, 2015.
CANDELiS, ImageGrid™: Image Management Appliance, 6 page color brochure. (AD-012 Rev. F Nov. 2012), © 2012 Candelis, Inc. Downloaded from http://www.candelis.com/images/pdf/Candelis_ImageGrid_Appliance_20111121.pdf. Accessed on Feb. 9, 2015.
Carestream, Cardiology PACS, 8 page color brochure. (CAT 866 6075 Jun. 2012). © Carestream Health, Inc., 2012. Downloaded from http://www.carestream.com/cardioPACS_brochure_M1-877.pdf. Accessed on Feb. 9, 2015.
Carestream, Vue PACS, 8 page color brochure. (CAT 300 1035 May 2014). © Carestream Health, Inc., 2014. Downloaded from http://www.carestream.com/csPACS_brochure_M1-876.pdf. Accessed on Feb. 9, 2015.
Cerner, Radiology—Streamline image management, 2 page color brochure, (fl03_332_10_v3). Downloaded from http://www.cerner.com/uploadedFiles/Clinical_Imaging.pdf. Accessed on Feb. 9, 2015.
CoActiv, EXAM-PACS, 2 page color brochure, © 2014 CoActiv, LLC. Downloaded from http://coactiv.com/wp-content/uploads/2013/08/EXAM-PACS-BROCHURE-final-web.pdf. Accessed on Feb. 9, 2015.
Crowley, Rebecca et al., Development of Visual Diagnostic Expertise in Pathology: an Information-processing Study, Jan. 2003, Journal of the American medical Informatics Association, vol. 10, No. 1, pp. 39-51.
DR Systems, Dominator™ Guide for Reading Physicians, Release 8.2, 546 pages, (TCP-000260-A), © 1997-2009, DR Systems, Inc. Downloaded from https://resources.dominator.com/assets/004/6999.pdf. Document accessed Feb. 9, 2015.
DR Systems, DR Scheduler User Guide, Release 8.2, 410 pages, (TCP-000115-A), © 1997-2009, DR Systems, Inc. Downloaded from https://resources.dominator.com/assets/003/6850.pdf. Document accessed Feb. 9, 2015.
Erickson, et al.: "Effect of Automated Image Registration on Radiologist Interpretation," Journal of Digital Imaging, vol. 20, No. 2 Jun. 2007; pp. 105-113.
Erickson, et al.: "Image Registration Improves Confidence and Accuracy of Image Interpretation," Special Issue-Imaging Informatics, Cancer Informatics 2007: 1 19-24.
Fujifilm Medical Systems, SYNAPSE® Product Data, Synapse Release Version 3.2.1, Foundation Technologies, 4 page color brochure, (XBUSSY084) Aug. 2008. Downloaded from http://www.fujifilmusa.com/shared/bin/foundation.pdf. Accessed on Feb. 9, 2015.
Fujifilm Medical Systems, SYNAPSE® Product Data, Synapse Release Version 3.2.1, Server Modules and Interfaces, 4 page color brochure, (XBUSSY085) Aug. 2008. Downloaded from http://www.fujifilmusa.com/shared/bin/server-interface.pdf. Accessed on Feb. 9, 2015.
Fujifilm Medical Systems, SYNAPSE® Product Data, Synapse Release Version 3.2.1, Workstation Software, 4 page color brochure, (XBUSSY082) Aug. 2008. Downloaded from http://www.fujifilmusa.com/shared/bin/workstation.pdf. Accessed on Feb. 9, 2015.
GE Healthcare, Centricity PACS, in 8 page printout. Accessed at http://www3.gehealthcare.com/en/products/categories/healthcare_it/medical_imaging_informatics_-_ris-pacs-cvis/centricity_pacs. Accessed on Feb. 9, 2015.
Handylife.com—Overview of Handy Patients Enterprise, in 2 page printout. Accessed from http://www.handylife.com/en/software/overview.html. Accessed on Feb. 18, 2015.
Handylife.com—Features of Handy Patients Enterprise, in 4 page printout. Accessed from http://www.handylife.com/en/software/features.html. Accessed on Feb. 18, 2015.
Handylife.com—Screenshots of Handy Patients Enterprise, in 2 page printout. Accessed from http://www.handylife.com/en/software/screenshots.html. Accessed on Feb. 18, 2015.
iCRco, I See the Future, in 12 pages, color brochure, (BR080809AUS), © 2009 iCRco.ClarityPACS. Downloaded from http://www.claritypacs.com/pdfs/ISeeFuture_26_Web.pdf. Accessed on Feb. 9, 2015.
Imageanalysis, dynamika, 2 page color brochure. Downloaded from http://www.imageanalysis.org.uk/what-we-do. Accessed on Feb. 9, 2015.
Imageanalysis, MRI Software, in 5 page printout. Accessed at http://www.imageanalysis.org.uk/mri-software. Accessed on Feb. 9, 2015.
IMSI, Integrated Modular Systems, Inc., Hosted / Cloud PACS in one page printout. Accessed at http://www.imsimed.com/#!products-services/ctnu. Accessed on Feb. 9, 2015.
Infinitt, PACS, RIS, Mammo PACS, Cardiology Suite and 3D/Advanced Visualization | Infinittna, 2 page printout. Accessed at http://www.infinittna.com/products/radiology/radiology-pacs. Accessed on Feb. 9, 2015.
Intelerad, IntelePACS, 2 page color brochure, © 2014 Intelerad Medical Systems Incoprorated. Downloaded http://www.intelerad.com/wp-content/uploads/sites/2/2014/08/IntelePACS-brochure.pdf. Accessed on Feb. 9, 2015.
Intelerad, InteleViewer, 2 page color brochure, © 2014 Intelerad Medical Systems Incoprorated. Downloaded from http://www.intelerad.com/wp-content/uploads/sites/2/2014/09/InteleViewer-brochure.pdf. Accessed on Feb. 9, 2015.
Intuitive Imaging Informatics, ImageQube, 1 page in color. Downloaded from http://www.intuitiveimaging.com/2013/pdf/ImageQube%20one-sheet.pdf. Accessed on Feb. 9, 2015.
Kuhl, Helen: Comparison Chart/PACS, Customers Are Happy, But Looking for More, (color) Imaging Techology News, itnonline.com, May 2012, pp. 24-27. Downloaded from http://www.merge.com/MergeHealthcare/media/company/In%20The%20News/merge-pacs-comparison.pdf. Accessed on Feb. 9, 2015.
LUMEDX CardioPACS 5.0 Web Viewer, Cardiopacs Module, 2 page color brochure, (506-10011 Rev A). Downloaded from http://cdn.medicexchange.com/images/whitepaper/cardiopacs_web_viewer.pdf?1295436926. Accessed on Feb. 9, 2015.

(56) References Cited

OTHER PUBLICATIONS

LUMEDX Cardiovascular Information System, CardioPACS, one page in color printout. Accessed at http://www.lumedx..com/pacs.aspx. Accessed on Feb. 9, 2015.
McKesson Enterprise Medical Imagining and PACS | McKesson, 1 page (color) printout. Accessed at http://www.mckesson.com/providers/health-systems/diagnostic-imaging/enterprise-medical-imaging. Accessed on Feb. 9, 2015.
Medweb Radiology Workflow Solutions, Radiology Workflow Solutions, Complete Workflow & Flexible Turnkey Solutions, Web RIS/PACS with Advanced Viewer, 3 page color brochure, © 2006-2014 Medweb. Downloaded from http://www.medweb.com/docs/rispacs_brochure_2014.pdf. Accessed on Feb. 9, 2015.
Mendelson, et al., "Informatics in Radiology—Image Exchange: IHE and the Evolution of Image Sharing," RadioGraphics, Nov.-Dec. 2008, vol. 28, No. 7.
Merge Radiology Solutions, Merge PACS, A real-time picture archiving communication system, (PAX-21990 rev 2.0), 2 page color brochure. Downloaded from http://www.merge.com/MergeHealthcare/media/documents/brochures/Merge_PACS_web.pdf. Accessed on Feb. 9, 2015.
NOVARAD Enterprise Imaging Solutions, NOVAPACS, 2 page (color) printout. Accessed at http://ww1.novarad.net/novapacs. Accessed on Feb. 9, 2015.
PACSPLUS, PACSPLUS Server, 1 page (color) printout. Accessed at http://www.pacsplus.com/01_products/products_01.html. Accessed on Feb. 9, 2015.
PACSPLUS, PACSPLUS Workstation, 3 page (color) printout. Accessed at http://www.pacsplus.com/01_products/products_01.html. Accessed on Feb. 9, 2015.
Philips IntelliSpace PACS, in 2 color page printout. Accessed at https://www.healthcare.philips.com/main/products/healthcare_informatics/products/enterprise_imaging_informatics/isite_pacs. Accessed on Feb. 9, 2015.
Philips, IntelliSpace: Multi-modality tumor tracking application versus manual PACS methods, A time study for Response Evaluation Criteria in Solid Tumors (RECIST). 2012, Koninklijke Philips Electronics N.V., in four pages.
RamSoft, RIS PACS Teleradiology, PowerServer PACS, Lite PACS, XU PACS Compare RamSoft Pacs Products, 2 color page printout. Accessed at http://www.ramsoft.com/products/powerserver-pacs-overview. Accessed on Feb. 9, 2015.
Rosset et al.: "OsiriX: An Open-Source Software for Navigating in Multidimensional DICOM Images," Journal of digital Imaging, Sep. 2004, pp. 205-216.
Sage Intergy PACS | Product Summary. Enhancing Your Workflow by Delivering Web-based Diagnostic Images When and Where You Need Them, in 2 color pages. (IRV-SS-INTPACS-PSS-031309). © 2009 Sage Software Healcare, Inc. Downloaded from http://www.greenwayhealth.com/solutions/intergy/. Accessed on Feb. 9, 2015.
Schellingerhout, Dawid, MD, et al.: "Coregistration of Head CT Comparison Studies: Assessment of Clinical Utility," Acad Radiol 2003; 10:242-248.
ScImage, Cardiology PACS, in 8 color page printout. Accessed at http://www.scimage.com/solutions/clinical-solutions/cardiology. Accessed on Feb. 9 2015.
Sectra RIS PACS, in 2 color page printout. Accessed at https://www.sectra.com/medical/diagnostic_imaging/solutions/ris-pacs/. Accessed on Feb. 9, 2015.
Siemens syngo.plaza, Features and Benefits, in 2 color page printout. Accessed at http://www.healthcare.siemens.com/medical-imaging-it/imaging-it-radiology-image-management-pacs/syngoplaza/features. Accessed on Feb. 9, 2015.
Simms | RIS and PACS Medical Imaging Software, in 2 color page printout. http://www.mysimms.com/ris-pacs.php. Accessed on Feb. 9, 2015.
Stryker, Imaging—OfficePACS Power Digital Imaging, in one color page printout. Accessed from http://www.stryker.com/emea/Solutions/Imaging/OfficePACSPowerDigitalImaging/index.htm. Accessed on Feb. 9, 2015.
Stryker, OfficePACS Power—Digital Imaging, 8 page color brochure, (MPP-022 Rev 4 BC/MP 300 Jan. 2007). © 2007 Stryker. Downloaded from http://www.stryker.com/emea/Solutions/Imaging/OfficePACSPowerDigitalImaging/ssLINK/emea/1557/022268. Accessed on Feb. 9, 2015.
UltraRAD—ultra Vision, 1 page (color). Downloaded from http://www.ultraadcorp.com/pdf/UltraVISION.pdf. Accessed on Feb. 9, 2015.
VioStream for VitreaView, 2 color pages printout. Accessed at http://www.vitalimages.com/solutions/universal-viewing/viostream-for-vitreaview. Accessed on Feb. 9, 2015.
Visage Imaging Visage 7, 3 color page printout. Accessed at http://www.visageimaging.com/visage-7. Accessed on Feb. 9, 2015.
VIZTEK Radiology PACS Software Vixtek Opal-RAD, 4 color page printout. Accessed at http://viztek.net/products/opal-rad. Accessed on Feb. 9, 2015.
Voyager Imaging—Voyager PACS Radiologist Workstation, 2 page color brochure. Downloaded from http://www.intellirad.com.au/assets/Uploads/Voyager-PacsWorkstations.pdf?. Accessed on Feb. 9, 2015.
Voyager Imaging—Voyager PACS, 3 page color brochure. Downloaded from http://www.intellirad.com.au/index.php/assets/Uploads/Voyager-Pacs3.pdf. Accessed on Feb. 9, 2015.
Ivetic, D., and Dragan, D., Medical Image on the Go!, 2009, J Med Syst, vol. 35, pp. 499-516.
Tahmoush, D. and Samet, H., A New Database for Medical Images and Information, 2007, Medical Imaging 2007; PACS and Imaging Informatics, vol. 6516. pp. 1-9.
U.S. Appl. No. 15/292,006, Systems and Methods for Viewing Medical 3D Imaging Volumes, filed Oct. 12, 2016.
U.S. Appl. No. 15/346,530, Systems and Methods for Matching, Naming, and Displaying Medical Images, filed Nov. 8, 2016.
U.S. Appl. No. 15/292,023, Selective Display of Medical Images, filed Oct. 12, 2016.
U.S. Appl. No. 15/188,872, Intelligent Management of Computerized Advanced Processing, filed Jun. 21, 2016.
U.S. Appl. No. 15/188,819, Intelligent Management of Computerized Advanced Processing, filed Jun. 21, 2016.
Office Action dated Jan. 17, 2017, in U.S. Appl. No. 14/540830.
Office Action dated Dec. 12, 2016, in U.S. Appl. No. 15/254,627.
Corrected Notice of Allowance dated Oct. 21, 2016 in U.S. Appl. No. 14/081,225.
Corrected Notice of Allowance dated Nov. 16, 2016 in U.S. Appl. No. 14/244,431.
Appeal Brief dated Jul. 15, 2016 in U.S. Appl. No. 14/043,165.
Examiner's Answer dated Nov. 14, 2016, in U.S. Appl. No. 14/043,165.
Office Action, dated Jan. 12, 2017 in U.S. Appl. No. 15/292,023.
Restriction Requirement, dated Jul. 28, 2015 in U.S. Appl. No. 14/139,068.
Office Action, dated Mar. 11, 2016 in U.S. Appl. No. 14/139,068.
Notice of Allowance, dated Sep. 21, 2016 in U.S. Appl. No. 14/139,068.
Sprawls, "Image Characteristics and Quality," Physical Principles of Medical Imaging, http://www.sprawls.org/resources pp. 1-14.
TeraRecon iNtuition pamphlet in 20 pages, retrieved on Nov. 8, 2013, available at http://int.terarecon.com/wp-content/uploads/2013/11/brochure_english2013.pdf.
TeraRecon iNtuition—Workflow. <www.terarecon.com/wordpress/our-solutions/intuition-workflow> Last accessed Nov. 8, 2013. 2 pages.
Bergstrom, Patrik, "Automated setup of display protocols." (2015).
Sprawls, P. "Image Characteristics and Quality" Physical Principles of Medical Imaging, ttp://www.sprawls.org/resources ' Date not available.
Advisory Action from the U.S. Patent and Trademark Office for U.S. Appl. No. 11/179,384 dated Sep. 17, 2009 (3 pages).
Interview Summary from the U.S. Patent and Trademark Office for U.S. Appl. No. 11/179,384 dated Feb. 18, 2009 (2 pages).
Interview Summary from the U.S. Patent and Trademark Office for U.S. Appl. No. 11/179,384 dated Sep. 24, 2008 (2 pages).
Notice of Allowance from the U.S. Patent and Trademark Office for U.S. Appl. No. 11/265,979 dated May 13, 2011 (14 pages).

(56) References Cited

OTHER PUBLICATIONS

Interview Summary from the U.S. Patent and Trademark Office for U.S. Appl. No. 11/942,687 dated Jun. 10, 2011 (4 pages).
Patent Board Decision from the U.S. Patent and Trademark Office for U.S. Appl. No. 11/942,687 dated Dec. 22, 2017 (13 pages).
Advisory Action from the U.S. Patent and Trademark Office for U.S. Appl. No. 11/944,000 dated Aug. 1, 2011 (3 pages).
Interview Summary from the U.S. Patent and Trademark Office for U.S. Appl. No. 11/944,000 dated Feb. 4, 2011 (3 pages).
Non-Final Office Action from the U.S. Patent and Trademark Office for U.S. Appl. No. 11/944,000 dated Oct. 5, 2012 (11 pages).
Notice of Allowance from the U.S. Patent and Trademark Office for U.S. Appl. No. 11/944,000 dated Jan. 30, 2017 (11 pages).
Examiner-Initiated Interview Summary from the U.S. Patent and Trademark Office for U.S. Appl. No. 12/857,915 dated Jul. 3, 2014 (1 pages).
Interview Summary from the U.S. Patent and Trademark Office for U.S. Appl. No. 12/870,645 dated Jun. 10, 2011 (3 pages).
Notice of Allowance from the U.S. Patent and Trademark Office for U.S. Appl. No. 12/870,645 dated Sep. 13, 2011 (8 pages).
Examiner-Initiated Interview Summary from the U.S. Patent and Trademark Office for U.S. Appl. No. 12/891,543 dated Nov. 14, 2013 (1 pages).
Notice of Allowance from the U.S. Patent and Trademark Office for U.S. Appl. No. 12/891,543 dated Nov. 14, 2013 (13 pages).
Examiner-Initiated Interview Summary from the U.S. Patent and Trademark Office for U.S. Appl. No. 13/171,081 dated Sep. 4, 2013 (1 pages).
Corrected Notice of Allowability from the U.S. Patent and Trademark Office for U.S. Appl. No. 13/572,397 dated Jun. 29, 2015 (2 pages).
Applicant-Initiated Interview Summary from the U.S. Patent and Trademark Office for U.S. Appl. No. 13/768,765 dated Jun. 11, 2015 (3 pages).
Examiner-Initiated Interview Summary from the U.S. Patent and Trademark Office for U.S. Appl. No. 13/768,765 dated Aug. 28, 2015 (1 pages).
Non-Final Office Action from the U.S. Patent and Trademark Office for U.S. Appl. No. 13/768,765 dated Mar. 17, 2015 (17 pages).
Advisory Action from the U.S. Patent and Trademark Office for U.S. Appl. No. 13/907,128 dated Dec. 13, 2013 (2 pages).
Advisory Action from the U.S. Patent and Trademark Office for U.S. Appl. No. 14/043,165 dated Jul. 9, 2015 (2 pages).
Non-Final Office Action from the U.S. Patent and Trademark Office for U.S. Appl. No. 14/043,165 dated Oct. 14, 2014 (18 pages).
Notice of Allowance from the U.S. Patent and Trademark Office for U.S. Appl. No. 14/043,165 dated Aug. 6, 2018 (11 pages).
Notice of Allowance from the U.S. Patent and Trademark Office for U.S. Appl. No. 14/043,165 dated Mar. 19, 2018 (11 pages).
Patent Board Decision from the U.S. Patent and Trademark Office for U.S. Appl. No. 14/043,165 dated Dec. 20, 2017 (11 pages).
Notice of Allowance from the U.S. Patent and Trademark Office for U.S. Appl. No. 14/095,123 dated Mar. 30, 2017 (10 pages).
Applicant-Initiated Interview Summary from the U.S. Patent and Trademark Office for U.S. Appl. No. 14/179,328 dated Dec. 11, 2014 (3 pages).
Notice of Allowance from the U.S. Patent and Trademark Office for U.S. Appl. No. 14/298,806 dated Apr. 12, 2017 (10 pages).
Applicant-Initiated Interview Summary from the U.S. Patent and Trademark Office for U.S. Appl. No. 14/540,830 dated Jul. 28, 2017 (3 pages).
Applicant-Initiated Interview Summary from the U.S. Patent and Trademark Office for U.S. Appl. No. 14/540,830 dated Mar. 24, 2017 (3 pages).
Final Office Action from the U.S. Patent and Trademark Office for U.S. Appl. No. 14/540,830 dated May 15, 2017 (42 pages).
Notice of Allowance from the U.S. Patent and Trademark Office for U.S. Appl. No. 14/540,830 dated Aug. 15, 2017 (8 pages).
Final Office Action from the U.S. Patent and Trademark Office for U.S. Appl. No. 14/792,210 dated Mar. 5, 2019 (17 pages).
Non-Final Office Action from the U.S. Patent and Trademark Office for U.S. Appl. No. 14/792,210 dated Aug. 27, 2018 (15 pages).
Corrected Notice of Allowability from the U.S. Patent and Trademark Office for U.S. Appl. No. 14/792,210 dated Sep. 5, 2019 (2 pages).
Notice of Allowance from the U.S. Patent and Trademark Office for U.S. Appl. No. 14/792,210 dated Jun. 17, 2019 (10 pages).
Non-Final Office Action from the U.S. Patent and Trademark Office for U.S. Appl. No. 15/140,346 dated May 28, 2019 (39 pages).
Non-Final Office Action from the U.S. Patent and Trademark Office for U.S. Appl. No. 15/140,348 dated Jul. 9, 2019 (21 pages).
Non-Final Office Action from the U.S. Patent and Trademark Office for U.S. Appl. No. 15/140,348 dated Nov. 19, 2018 (33 pages).
Advisory Action from the U.S. Patent and Trademark Office for U.S. Appl. No. 15/140,351 dated Mar. 5, 2019 (3 pages).
Examiner-Initiated Interview Summary from the U.S. Patent and Trademark Office for U.S. Appl. No. 15/140,351 dated Mar. 5, 2019 (1 pages).
Applicant-Initiated Interview Summary from the U.S. Patent and Trademark Office for U.S. Appl. No. 15/140,351 dated Jul. 15, 2019 (3 pages).
Final Office Action from the U.S. Patent and Trademark Office for U.S. Appl. No. 15/140,351 dated Dec. 6, 2018 (21 pages).
Non-Final Office Action from the U.S. Patent and Trademark Office for U.S. Appl. No. 15/140,351 dated May 21, 2019 (14 pages).
Non-Final Office Action from the U.S. Patent and Trademark Office for U.S. Appl. No. 15/140,351 dated Jul. 30, 2018 (25 pages).
Non-Final Office Action from the U.S. Patent and Trademark Office for U.S. Appl. No. 15/140,363 dated Jun. 3, 2019 (33 pages).
Examiner-Initiated Interview Summary from the U.S. Patent and Trademark Office for U.S. Appl. No. 15/163,600 dated Sep. 14, 2016 (1 pages).
Applicant-Initiated Interview Summary from the U.S. Patent and Trademark Office for U.S. Appl. No. 15/188,819 dated Sep. 24, 2018 (4 pages).
Non-Final Office Action from the U.S. Patent and Trademark Office for U.S. Appl. No. 15/188,819 dated Jul. 3, 2018 (7 pages).
Notice of Allowance from the U.S. Patent and Trademark Office for U.S. Appl. No. 15/188,819 dated Aug. 21, 2019 (8 pages).
Notice of Allowability from the U.S. Patent and Trademark Office for U.S. Appl. No. 15/188,819 dated Mar. 15, 2019 (5 pages).
Notice of Allowance from the U.S. Patent and Trademark Office for U.S. Appl. No. 15/188,819 dated Jan. 25, 2019 (7 pages).
Applicant-Initiated Interview Summary from the U.S. Patent and Trademark Office for U.S. Appl. No. 15/188,872 dated Jul. 15, 2019 (4 pages).
Final Office Action from the U.S. Patent and Trademark Office for U.S. Appl. No. 15/188,872 dated May 8, 2019 (14 pages).
Non-Final Office Action from the U.S. Patent and Trademark Office for U.S. Appl. No. 15/188,872 dated Oct. 19, 2018 (12 pages).
Corrected Notice of Allowability from the U.S. Patent and Trademark Office for U.S. Appl. No. 15/254,627 dated Jul. 13, 2017 (4 pages).
Notice of Allowance from the U.S. Patent and Trademark Office for U.S. Appl. No. 15/254,627 dated Apr. 3, 2017 (11 pages).
Examiner-Initiated Interview Summary from the U.S. Patent and Trademark Office for U.S. Appl. No. 15/292,006 dated Nov. 29, 2018 (1 pages).
Final Office Action from the U.S. Patent and Trademark Office for U.S. Appl. No. 15/292,006 dated Oct. 17, 2018 (18 pages).
Non-Final Office Action from the U.S. Patent and Trademark Office for U.S. Appl. No. 15/292,006 dated May 9, 2018 (17 pages).
Corrected Notice of Allowability from the U.S. Patent and Trademark Office for U.S. Appl. No. 15/292,006 dated Sep. 4, 2019 (3 pages).
Corrected Notice of Allowability from the U.S. Patent and Trademark Office for U.S. Appl. No. 15/292,006 dated Aug. 22, 2019 (3 pages).
Notice of Allowance from the U.S. Patent and Trademark Office for U.S. Appl. No. 15/292,006 dated Aug. 7, 2019 (6 pages).
Notice of Allowance from the U.S. Patent and Trademark Office for U.S. Appl. No. 15/292,006 dated Apr. 10, 2019 (6 pages).

(56) References Cited

OTHER PUBLICATIONS

Corrected Notice of Allowability from the U.S. Patent and Trademark Office for U.S. Appl. No. 15/292,006 dated Jan. 28, 2019 (3 pages).
Notice of Allowance from the U.S. Patent and Trademark Office for U.S. Appl. No. 15/292,006 dated Nov. 29, 2018 (12 pages).
Notice of Allowance from the U.S. Patent and Trademark Office for U.S. Appl. No. 15/292,023 dated Apr. 11, 2017 (11 pages).
Advisory Action from the U.S. Patent and Trademark Office for U.S. Appl. No. 15/346,530 dated Nov. 21, 2018 (4 pages).
Applicant-Initiated Interview Summary from the U.S. Patent and Trademark Office for U.S. Appl. No. 15/346,530 dated May 17, 2018 (3 pages).
Final Office Action from the U.S. Patent and Trademark Office for U.S. Appl. No. 15/346,530 dated Sep. 6, 2018 (14 pages).
Non-Final Office Action from the U.S. Patent and Trademark Office for U.S. Appl. No. 15/346,530 dated Mar. 26, 2018 (12 pages).
Notice of Allowance from the U.S. Patent and Trademark Office for U.S. Appl. No. 15/346,530 dated Aug. 27, 2019 (7 pages).
Notice of Allowance from the U.S. Patent and Trademark Office for U.S. Appl. No. 15/346,530 dated May 15, 2019 (8 pages).
Notice of Allowance from the U.S. Patent and Trademark Office for U.S. Appl. No. 15/188,872 dated Aug. 23, 2019 (10 pages).
Final Office Action from the U.S. Patent and Trademark Office for U.S. Appl. No. 15/140,346 dated Oct. 31, 2019 (41 pages).
Non-Final Office Action from the U.S. Patent and Trademark Office for U.S. Appl. No. 15/140,348 dated Dec. 4, 2019 (21 pages).
Final Office Action from the U.S. Patent and Trademark Office for U.S. Appl. No. 15/140,351 dated Nov. 14, 2019 (14 pages).
Supplemental Notice of Allowability from the U.S. Patent and Trademark Office for U.S. Appl. No. 15/188,819 dated Oct. 2, 2019 (4 pages).
Supplemental Notice of Allowability from the U.S. Patent and Trademark Office for U.S. Appl. No. 15/188,872 dated Oct. 28, 2019 (5 pages).
Corrected Notice of Allowability from the U.S. Patent and Trademark Office for U.S. Appl. No. 15/292,006 dated Dec. 12, 2019 (3 pages).
Corrected Notice of Allowability from the U.S. Patent and Trademark Office for U.S. Appl. No. 15/346,530 dated Dec. 17, 2019 (8 pages).
Notice of Allowance from the U.S. Patent and Trademark Office for U.S. Appl. No. 14/792,210 dated Oct. 11, 2019 (9 pages).

* cited by examiner

Exam Title: Pelvic Ultrasound
Date: 11/15/2008
Comparison Exams: None

Family History: Mother with history of ovarian cancer.
Menstrual History: Irregular menstrual periods with abnormal bleeding
Technique: Standard transpelvic and endovaginal technique performed Findings:
Uterus: Size is enlarged.
Ovaries: The left ovary is present.

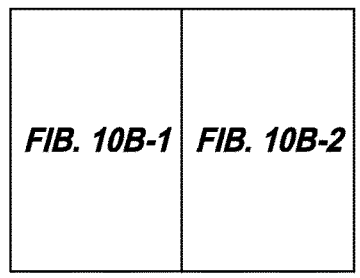
FIB. 10B
FIG. 10B-1
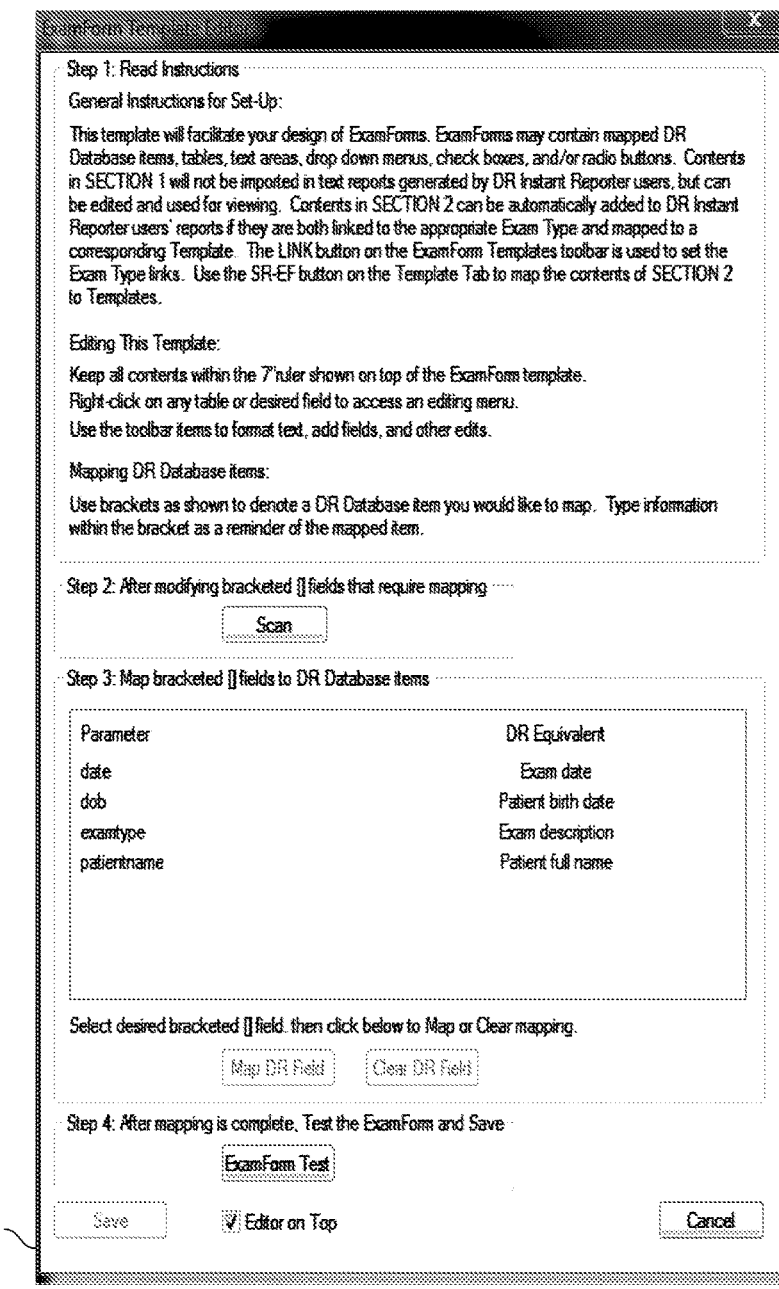

FIG. 10B-2

SECTION 1: Exam Information —— 1014

Patient Name: [patientname]
Exam Type: [examtype]     1020
Date of Birth: [dob]
Date: [date]

INSTRUCTION: Please follow technique specified in the DR Default Protocol. Complete the Indications field with the patients signs, symptoms, or other referral information. Avoid abbreviations. Type neatly, and punctuate properly.

PATIENT FAQ's:
When will the report be ready? If the patient asks, respond by inquiring if they have any special needs. Please inform the patient that although we create reports promptly, their doctor may need time to receive other results and consider their condition further, so that it is best to wait for their next follow-up appointment or follow other instructions received from their doctor, rather than calling their doctor immediately. If the patient has special reporting needs, please indicate below and notify the reading physician on duty.

How can the patient obtain their images/results? The quickest and easiest is via the Internet using eMix. If the patient desires this option, complete the eMix Request Task and verify that we have the correct patient email address in Patient Properties. The patient will receive an email notification from us when the results are ready, and will be able to confidentially access images and reports, as well as create a CD. Alternatively, we can create a CD for the patient that may not yet include the report (the patient can wait or return later to pick up).

How does the referring access results? Most referring physicians can access results confidentially via the Internet. Physicians who do not have rights to do so (such as those outside of this medical community) can use eMix.

Technologist Note:     1018

SECTION 2: Auto-Import Note —— 1016

1012

| EXAM DATA: | | | (Normal) |
|---|---|---|---|
| Aortic Root Diameter: | | cm | (2.0-3.7 cm) |
| Left Ventricular Diameter | | | |
| Diastole: | 1022 | cm | (3.7 - 5.6 cm) |
| Systole: | | cm | (1.8 - 4.2 cm) |

FIG. 10C

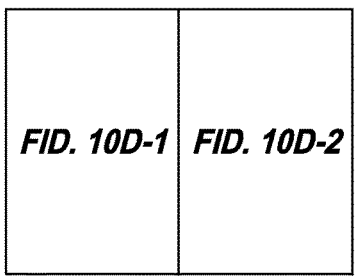
FID. 10D
FIG. 10D-1
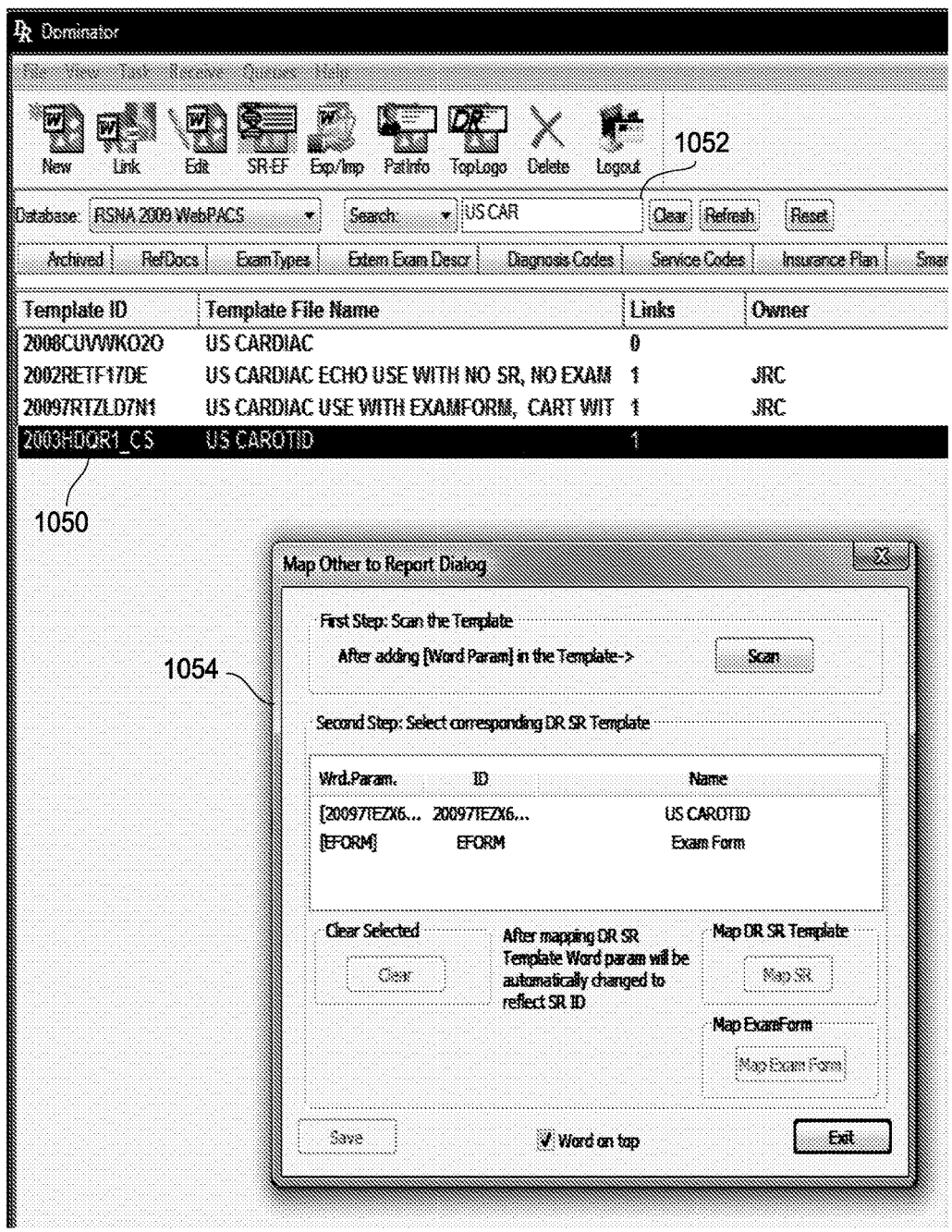

FIG. 10D-2

PROCEDURE: COLOR DUPLEX DOPPLER CAROTID ULTRASOUND

COMPARISON: None.

INDICATIONS:

TECHNIQUE: Color duplex Doppler ultrasound and pulsed Doppler analysis were performed to evaluate the cervical carotid arteries and vertebral flow.

FINDINGS:
[20097TEZX6BW7] 1048
[EFORM]
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
Spectral Doppler US Thresholds (Reference: Grant EG, et al. Radiology 2000; 214:247-252)

| Stenosis (%) | PSV (cm/sec) | VICA/VCCA |
|---|---|---|
| 0-49 | <150 | <2.5 |
| 50-69 | 150-225 | 2.5-4.0 |
| >70 | >225 | >4.0 | sd

Note for stented carotids: Velocity parameters are higher for stented arteries at same level of angiographic stenosis (Reference: Stanziale et al. J Endovasc Ther 2005: 12), as follows:
>50% stenosis (>225 cm/sec, >2.5 and >50% change from baseline post-stent exam)
>70% stenosis (>350 cm/sec, >4.75 and >50% from baseline)
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

CONCLUSION: WARNING: THIS REPORT WAS APPROVED PREMATURELY AND IS NOT ACCURATE. PLEASE CONTACT US IMMEDIATELY.

FIG. 10E

SECTION 1: Exam Information — 1062

Patient Name: COLLINS, MIA  ← 1060
Exam Type: CHEST AORTIC ANEURYSM W-
Date of Birth: 06/21/75
Date:         Oct-15-06

INSTRUCTION: Please follow technique specified in the DR Default Protocol. Complete the Indications field with the patients signs, symptoms, or other referral information. Avoid abbreviations. Type neatly, and punctuate properly.

THINK LOW DOSE: Consider limiting DLP to targets shown below for adults (mGy-cm):

| HEAD | NECK | CHEST | CHEST ANGIO | ABD | PELVIS | CACS | CORONARY |
|------|------|-------|-------------|-----|--------|------|----------|
| 870  | 1100 | 370   | 800         | 500 | 350    | 160  | 600      |

PATIENT FAQ's:
When will the report be ready? If the patient asks, respond by inquiring if they have any special needs. Please inform the patient that although we create reports promptly, their doctor may need time to receive other results and consider their condition further, so that it is best to wait for their next follow-up appointment or follow other instructions received from their doctor, rather than calling their doctor immediately. If the patient has special reporting needs, please indicate below and notify the reading physician on duty.

How can the patient obtain their images/results? The quickest and easiest is via the Internet using eMix. If the patient desires this option, complete the eMix Request Task and verify that we have the correct patient email address in Patient Properties. The patient will receive an email notification from us when the results are ready, and will be able to confidentially access images and reports, as well as create a CD. Alternatively, we can create a CD for the patient that might not include the report (the patient can wait or return later to pick up).

How does the referring access results? Most referring physicians can access results confidentially via the Internet. Physicians who do not have rights to do so (such as those outside of this medical community) can use eMix.

Technologist Note:

— 1064

SECTION 2: Auto-Import Note

CONTRAST TYPE/DOSE:   1066    [Omnipaque ▾]  cc.

DOSE-LENGTH PRODUCT (DLP):    mGy-cm

— 1068

Viewing 1 exam

FIG. 10F

Exam Form

Properties. The patient will receive an email notification from us when the results are ready, and will be able to confidentially access images and reports, as well as create a CD. Alternatively, we can create a CD for the patient (the patient can wait or return later to pick up).

How does the referring access results? Most referring physicians can access results confidentially via the Internet. Physicians who do not have rights to do so (such as those outside of this medical community) can use eMix.

Technologist Note:

Please call Dr. Jones.

Patient Remarks:

Patient leaving town on Tuesday.

---

SECTION 2: Auto-Import Note

| | |
|---|---|
| PERFORMED: | LEFT HEART CATH |
| SERVICE CODES: | 93510 |
| COMPARISON: | |
| DESCRIPTION: | After obtaining informed consent, the patient was brought to the cardiac catheterization laboratory. Patient monitoring included continuous pulse oximetry, EKG, and blood pressure recording as summarized below. |
| CONTRAST TYPE/DOSE: | Visipaque  145 cc. |
| MEDICATIONS GIVEN: | Versed I.V. 4 mg, Fentanyl I.V. 50 mcg. |
| APPROACH: | Left femoral artery. |
| DEVICES: | Cordis 6Fr sheath, Fr Boston Scientific sterible guidewire, Boston Scientific Taxus stent. |

Spell Check    Save

Viewing 1 exam

SYSTEM AND METHOD OF PROVIDING DYNAMIC AND CUSTOMIZABLE MEDICAL EXAMINATION FORMS

CROSS-REFERENCE TO RELATED APPLICATIONS

This application is a continuation of U.S. patent application Ser. No. 13/768,765, filed Feb. 15, 2013, which is a continuation of U.S. patent application Ser. No. 12/622,404, filed Nov. 19, 2009, which claims the benefit of U.S. Provisional Patent Application No. 61/116,191, filed on Nov. 19, 2008, the entire disclosure of which is incorporated by reference herein.

BACKGROUND

Field of the Invention

This application relates to the dynamic creation and customization of computer-based electronic forms which may be used for inputting, collecting, accessing, and presenting medical information.

Description of the Related Art

Existing medical examination forms do not optimally serve the needs of various users who frequently must collaborate to collect relevant clinical and demographic data, and ultimately compile this data for various purposes, including creation of medical reports, retrospectively analyzing the collected data, and uploading data to other repositories (such as clinical data repositories).

SUMMARY

The system, method, and devices described herein each have several aspects, no single one of which is solely responsible for its desirable attributes. Without limiting the scope of this disclosure, several non-limiting features will now be discussed briefly.

In a first embodiment, a method of providing an examination form is provided. The method includes storing a plurality of examination form templates. The examination form templates each comprise a plurality of data fields configured to receive data related to a medical examination. At least one data field is associated with a link to an external data source. The method further includes receiving a selection of one of the plurality of examination form templates and storing examination form template presentation rules. An instance of an examination form is generated based on the selected examination form template for display to a user. The generated instance is based at least in part on the template presentation rules. Data is automatically received into the examination form instance from one or more data sources based on the link, and user input is received which includes data which modifies information in the examination form. The modified examination form instance is stored in a memory, and information is exported from the examination form instance to one or more destinations.

In another embodiment, a method of producing a medical report using an electronically generated medical examination form is provided. The method includes receiving a request from a user for an examination form, the request comprising data indicative of selection criteria. The method further includes identifying one or more medical examination forms from a collection of medical examination forms based at least in part on the data indicative of the selection criteria. One or more of the medical examination forms are selected from the identified examinations forms, and an instance of the selected form is generated for display to the user. The method further includes receiving a plurality of data inputs into the medical examination form and automatically exporting the plurality of data inputs.

In another embodiment, a method of providing an examination form for collaboration between multiple users within a medical organization is provided. The method includes receiving a selection of an examination form template comprising a plurality of data fields configured to receive data related to a medical examination and to export data received into the form. The method further includes receiving indications of links between respective data fields of the examination form and respective data sources, the links comprising one or more import links and one or more export links. Data is automatically received into the examination form from one or more data sources based on the import links, and a first view of the examination form is generated for display to a first user having a first role. The first view is configured to receive data in a first subset of the data fields. The method further comprises receiving data input into at least some of the first subset of data fields of the first view of the examination form, and generating a second different view of the examination form for display to a second user having a second role, wherein the second view is configured to receive data in a second subset of the data fields, wherein the first subset of data fields includes at least one data field not included in the second subset of data fields. Data input into at least some of the second subset of data fields of the second view of the examination form is received. The method further includes determining one or more data fields associated with export links; and exporting data from the determined one or more fields to one or more locations.

In still another embodiment, a method of providing dynamic medical examination forms to provide efficient comparison of medical examination results is provided. The method includes storing a first medical examination form in a memory, the first medical examination form comprising one or more data fields having data associated with first imaging data generated for a first medical examination. The method further includes generating a second medical examination form based on the first medical form, the second medical form comprising the data fields and data from the first medical form, and further comprising additional data fields configured to receive data associated with second imaging data generated for a second medical examination. The first imaging data, the second imaging data, and the second medical form are concurrently displayed, and data associated with the second imaging data into the additional data fields is then received.

In still another embodiment, a system for creating dynamic medical examination forms is provided. The system comprises a first module configured to store a first medical examination form in a memory, the first medical examination form comprising one or more data fields having data associated with first imaging data generated for a first medical examination. The system further includes a second module configured to generate a second medical examination form based on the first medical form, the second medical form comprising the data fields and data from the first medical form, and further comprising additional data fields configured to receive data associated with second imaging data generated for a second medical examination. A third module is configured to display the first imaging data, the second imaging data, and the second medical form at the same time, and a fourth module is configured to receive data associated with the second imaging data into the additional data fields.

BRIEF DESCRIPTION OF THE DRAWINGS

FIG. 8E is an example of a graphical user interface of a report generated through the use of dynamic medical examination form software

FIGS. 10A, 10B (comprised of 10B-1 and 10B-2), 10C, 10D (comprised of 10D-1 and 10D-2), 10E, 10F, and 10G (comprised of 10G-1 and 10G-2) are examples of additional embodiments of graphical user interfaces used for creating and using dynamic medical examination forms and their associated reports.

DETAILED DESCRIPTION

Figure 1:
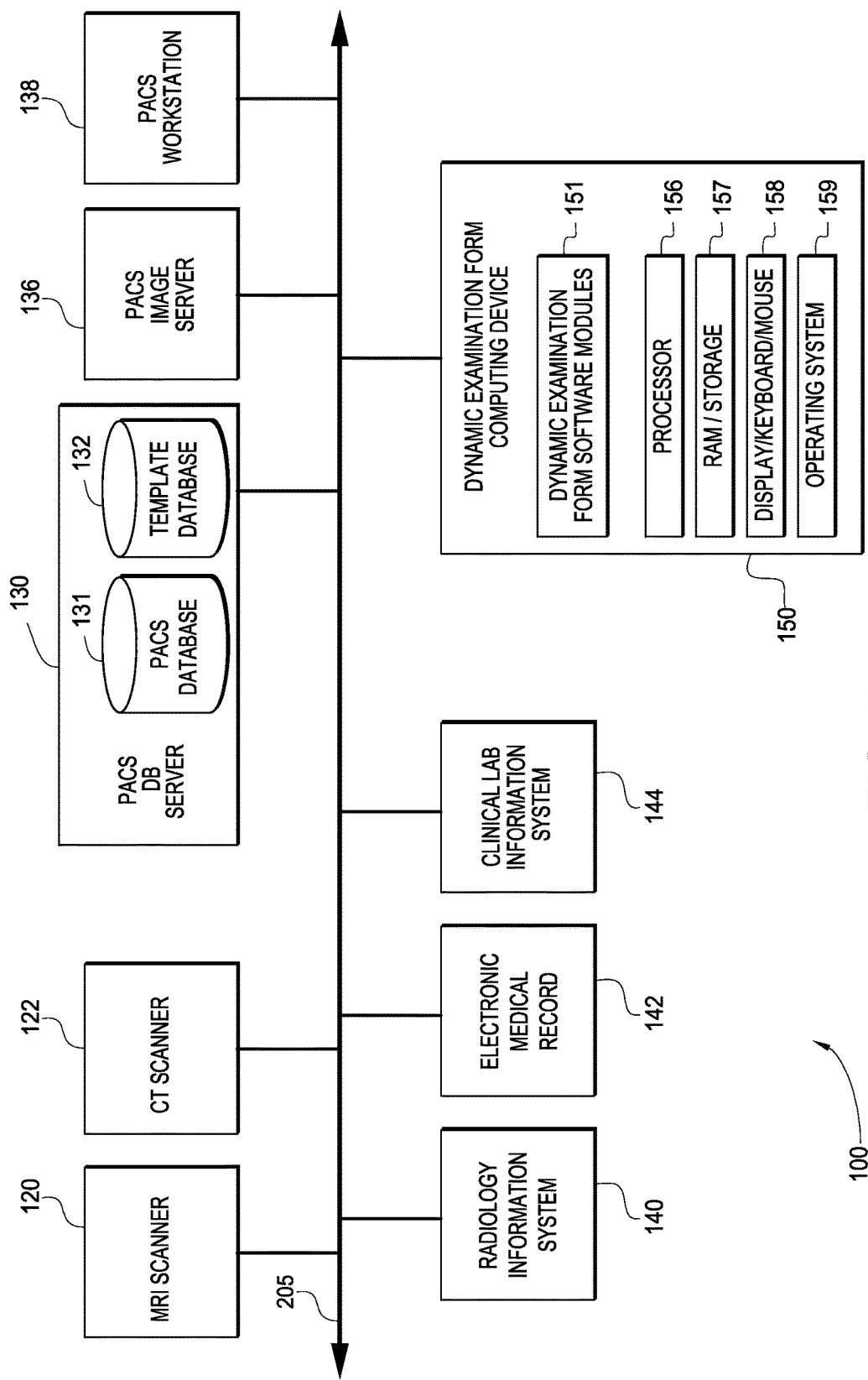
FIG. 1 is a system diagram which shows one embodiment of a system for creating dynamic and customizable medical examination forms.

One or more embodiments disclosed herein provide a system and method for providing dynamic and customizable medical examination forms. In certain specific embodiments, these dynamic and customizable medical forms may be automatically presented to users based on a predefined series of rules which allow multiple users having different roles in the clinical process to collaborate and contribute to a medical examination report, while at the same time maintaining an independent record of what was contributed and by whom it was contributed. For example, in certain embodiments, medical examination forms may be completed by a non-physician user such as a technologist. Some of that data may be automatically imported into a physician's reading report. However, in order to ensure reliability of data and to enable effective quality control measures, the examination forms may be associated with data which is indicative of who completed the form, when it was completed, who modified the form, and the like. Moreover, the medical examination forms disclosed herein may be subject to file protections which automatically (or manually) determines who can view, create, modify, delete, name, and/or link the medical examination forms.

The medical examination forms may contain text, graphics, and/or pictures. The medical examination forms may be used by various different parties having various different roles in an organization. For example, in the context of a medical practice, the medical examination forms may be used by a scheduler, a technician, a physician, or some other authorized user. Medical examination forms described herein may be created and/or used for various medical conditions, examination types, and the like. Moreover, certain medical examinations may involve the use of multiple examination forms.

The choice of which medical examination form to use for a particular situation may be manual or automatic and may be based on many different parameters. For a particular medical examination, there may be none, one, or more than one examination forms created. The choice of a medical examination form may be based on one or more of medical imaging modality, examination type, clinical history of the patient, demographic information about the patient, prior examinations, facility at which an exam is conducted, the type of scanner used for an imaging scan, the type of insurance a patient holds, the location of the patient, whether the patient inpatient or outpatient, indications for the examination, referring physician, referring physician attributes (such as specialty) and/or the requested reading physician (or reading physician attributes).

The medical examination forms may be configured to provide information fields that are pre-populated with designated information from various external data sources, including but not limited to PACS, EMR, HIS, clinical laboratory systems, prior medical reports, and the like. The external data sources may include systems provided by the same vendor as the examination forms, and the external data sources may also include systems provided by other vendors. Accordingly, an external data source may be any source of data or information that exists outside of the examination form itself. The dynamic medical examination forms may include fields that may receive updated data (e.g., in a subsequent patient examinations) regarding detected anomalies found in prior patient examinations. In some embodiments, the examination forms themselves may be updated during follow up examinations to include additional detected anomalies which were undetected during prior examinations. The updates to the examinations forms may include the addition of new fields or new links to external data made relevant by the additional detected anomalies. When an examination form has been completed, it may be exported to various different other systems. These systems may be systems provided by the same vendor as the examination forms. These other systems may also include systems provided by other vendors. For example, the medical examination forms and or various contents of the forms may be exported into a word processing document, an HL7 document, a PDF file, a database, an electronic medical record, a PACS system, or even a web-based registry or credentialing organization. Depending on the specific embodiment, the medical examination forms may or may not adhere to cross-enterprise document sharing (XDS), one of IHE technical frameworks, which describes how to apply standards into information systems for the sharing of medical documents among hospitals. Similarly they may or may not include the Clinical Document Architecture (CDA) schema based on HL7.

FIG. 1 is a system diagram which shows the various components of a system 100 for creating dynamic and customizable medical examination forms. As shown the system 100 may include a dynamic examination form computing device 150. The dynamic examination form computing device 150 may take various forms. In one embodiment, the dynamic examination form computing device 150 may be a computer workstation having dynamic examination form software modules 151. The dynamic examination form software modules 151 will be described in detail below. The computer workstation may be a standard personal computer running off-the-shelf operating systems 159 such as a Windows, Linux, or MacOS. The computer workstation 150 may also run a more specialized operating system which may be designed for the specific tasks performed by the computing device 150. In addition to taking the form of a desktop computer or workstation, the computing device 150 may be a laptop computer, a tablet computer, a notebook computer, a netbook computer, a handheld computing device, or some other type of computing device.

The dynamic examination computing device 150 may include one or more computing processors 156. The computer processors 156 may include central processing units (CPUs), and may further include dedicated processors such as graphics processor chips, and the like. The processors generally are used to execute computer instructions based on the dynamic examination form modules 151 to cause the computing device to perform operations as specified by the modules 151. The modules 151 may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. For example, modules may include software code written in a programming language, such as, for example, Java, Javascript, ActionScript, Visual Basic, Lua, C, C++, or C#. While "modules" are generally discussed herein with reference to software, any modules may alternatively be represented in hardware or firmware. Generally, the modules described herein refer to logical modules that may be combined with other modules or divided into sub-modules despite their physical organization or storage.

The dynamic examination computing device 150 may also include memory 157. The memory 157 may include volatile data storage such as RAM, SDRAM. The memory 157 may also include more permanent forms of storage such as a hard disk drive, a flash disk, a solid state drive, or some other type of non-volatile storage.

Also included in the dynamic examination computing device 150 may be various input and output devices 158 which receive information inputs and provide information from users. The input/output devices 158 may include a video display, such as one or more high-resolution computer monitors. The input/output devices 158 may also include a keyboard, mouse, touchscreen, microphone, voice command input system, and/or tablet, for example, that are configured to allow the user to provide input to the computing device 150.

The dynamic examination form computing device 150 may communicate and/or interface with other systems and/or devices. In one or more embodiments, the computer device 150 may be connected to a computer network 205. The computer network 205 may take various forms. It may be a wired network or a wireless network, or it may be some combination of both. The computer network 205 may be a single computer network, or it may be a combination or collection of different networks and network protocols. For example, the computer network 205 may include one or more local area network (LAN), wide area network (WAN), personal area network (PAN), and/or the Internet. Various devices and subsystems may be connected to the network 205. For example, one or more MRI scanners 120 may be connected to the network. The MRI scanner 120 may be used to acquire MRI images from patients, and may share the acquired images with other devices on the network 205. The network 205 may also include one or more CT scanners 122. The CT scanners 122 may also be used to acquire images and, like the MRI scanner device, may then store those images and/or share those images with other devices via the network 205. Any other scanner or device capable of inputting images could be included, including ultrasound, angiography, nuclear medicine, radiography, endoscopy, pathology, dermatology, etc.

Also connected to the network may be a picture archiving and communications system (PACS) database server 130. The PACS database server 130, along with PACS image server 136 (used to serve images in response to client requests) and PACS workstation 138 (used to provide a client interface to the PACS server components), form part of a PACS system. In some embodiments, the PACS database server 130 may include a PACS database which stores image data.

In the embodiment shown in FIG. 1, the PACS database server 130 also includes a dynamic examination form template database 132. In other embodiments the dynamic examination form template database 132 may be present in a different server, for example in a server accessible on the local LAN or in a server that is located remotely and accessible via the Internet. The dynamic examination form template database 132 stores examination form templates that have been created by the dynamic examination form software 151. These stored templates may be used to create new dynamic examinations forms as is discussed below.

The PACS system is typically used for the storage, retrieval, distribution and presentation of images (such as those created and/or generated by the MRI scanner 120 and CT Scanner 122). The medical images may be stored in an independent format, an open source format, or some other proprietary format. The most common format for image storage in the PACS system is the Digital Imaging and Communications in Medicine (DICOM) format. The stored images may be transmitted digitally via the PACS system, often reducing or eliminating the need for manually creating, filing, or transporting film jackets.

The network 205 may also be connected to a radiology information system 140. The radiology information system 140 is typically a computerized database system that is used by radiology departments to store, manipulate and distribute patient radiological data and imagery. Also attached to the network 205 may be an electronic medical record (EMR) system 142. The EMR system 142 may be configured to store and make accessible to a plurality of medical practitioners computerized medical records. Also attached to the network 205 may be a clinical laboratory information system 144. The clinical laboratory information system 144 is typically a software system which stores information created or generated by clinical laboratory process. In other embodiments, other computing devices that store, provide, acquire, and/or otherwise manipulate medical data may also be coupled to the network 205 and may be in communication with one or more of the devices illustrated in FIG. 1, such as with the examination form computing device 150.

As will be discussed in detail below, the dynamic medical examination form computing device 150 may be configured to interface with various networked computing devices in order to provide efficient and useful review of medical examination data that is stored among the various systems present in the network.

According to certain embodiments, dynamic medical examination forms may be provided which allow multiple users in the healthcare environment to collaborate to contribute data and information to a medical report in such a way that efficiencies are realized by assigning specific and/or limited tasks to each party involved in the medical documentation process. These efficiencies may be gained by providing a single dynamic medical examination form which (1) automatically receives data already known by some other entity in the system to avoid repetitious data entry; (2) automatically exports data inputted into the examination form to the external systems which require the data; and/or (3) provides appropriate access to each party involved in the creation of the medical examination form.

FIG. 1B is a block diagram illustrating a high-level view of the inputs and outputs from a medical examination form according to one or more embodiments. A medical examination form 170 may be connected to various data sources 180. The data sources 180 may be various different systems on the network 205, such as those described above in connection with FIG. 1A. According to certain embodiments, the dynamic medical examination form may be defined to automatically receive information from these data sources 180 based on presentation rules defined for the creation of the forms. For example, when a medical examination form is generated for a specific patient, a general presentation rule may indicate that the patient's demographic information be automatically brought into the medical examination form from an external patient database, such as the EMR 142. If the medical examination form is to be used for an MRI examination, for example, the MRI imaging data may be imported automatically into the form based on presentation rules for examination forms used in conjunction with MRI examinations.

For a given patient examination, many different types of data may be generated which may need to be sent to various different types of systems. For example, a report may need to be created by the physician specialist interpreting and reading a medical imaging examination so that the referring physician may be apprised of the examination outcome. Alternatively, or in addition, a report may also need to be created which allows the reading physician to easily find the data crucial to such a review. Additional data captured during the examination process (and in the medical examination form) may also need to be exported to an external system used for quality assurance, tracking of specific critical results, credentialing, data mining, inventory control, or medical billing system. These and other different systems and data repositories may receive some specified portion of the data entered into the examination form. Similarly, data repositories may receive only those data portions that are relevant to the respective repository, which may increase the efficiency and accuracy of the data repositories in properly categorizing the received data, and may reduce bandwidth needs since not all of the data is transmitted to all data repositories. In fact, each repository and/or group of repositories may be associated with delivery rules that indicate which portions of the data is transmitted to the repository. In the example shown in FIG. 1B, data received in the examination form 170 is sent to various data destinations 190. These data destinations may include a reading report 190, a billing system 192, a data repository 194, or some other data destination 196.

Because the different users and participants in the medical documentation process often play radically different roles in the information gathering and evaluation process, the medical examination form 170 may be configured to be presented in different ways to different users. In some embodiments, how a medical examination form 170 appears to a user may be predefined based on a series of rules that takes into account various attributes of the user, patient, exam, modality, location, etc. For example, the rules may be defined so that aspects of an examination form presented to a user may be dependent on the user's role within an organization. A technologist may see certain specific portions of the examination form, while a doctor may be presented with other portions of the form because each is responsible for entering and reviewing different data in the form. Each of the different presentations of a particular examination are referred to herein as "views" of the medical examination form. Thus, an examination form may have multiple views each based on a similar template, but each potentially importing different data, displaying different data, and/or exporting different data. In the example provided in FIG. 1B, various views are defined for the medical examination form 170: a physician view 172, a technologist view 174, a nurse view 176, and a billing view 178. While specific views based on personnel roles are shown in FIG. 1B, it is to be appreciated that different views may be defined based on almost any attribute. For example, a doctor may be presented with one view of the form before the actual associated medical examination takes place, while he may be presented with an entirely different view after the examination has taken place and a technologist has entered examination data.

In some embodiments, the different views may be used to protect or ensure the reliability of data entered into the medical examination form. For example, fields in a medical examination form may be designated as required data entry fields which prevent a user from saving an updated form unless they have entered appropriate data in the required data entry fields. Other fields may be protected from access or modification so that unauthorized users do not inadvertently (or even intentionally) change data in an examination form.

Alternatively, a single examination form may be presented to a single or various different intended users. As yet another alternative, a single examination form may be presented to various different users with different accessible or editable fields depending on the user, or other configurable conditions. Therefore, one can define a "view of an examination form" as an instance of an examination form created from an examination form template. One of more such views of an examination form can be presented during the life cycle of an examination, and in addition, there may be multiple different examination forms for any particular examination.

Figure 2:
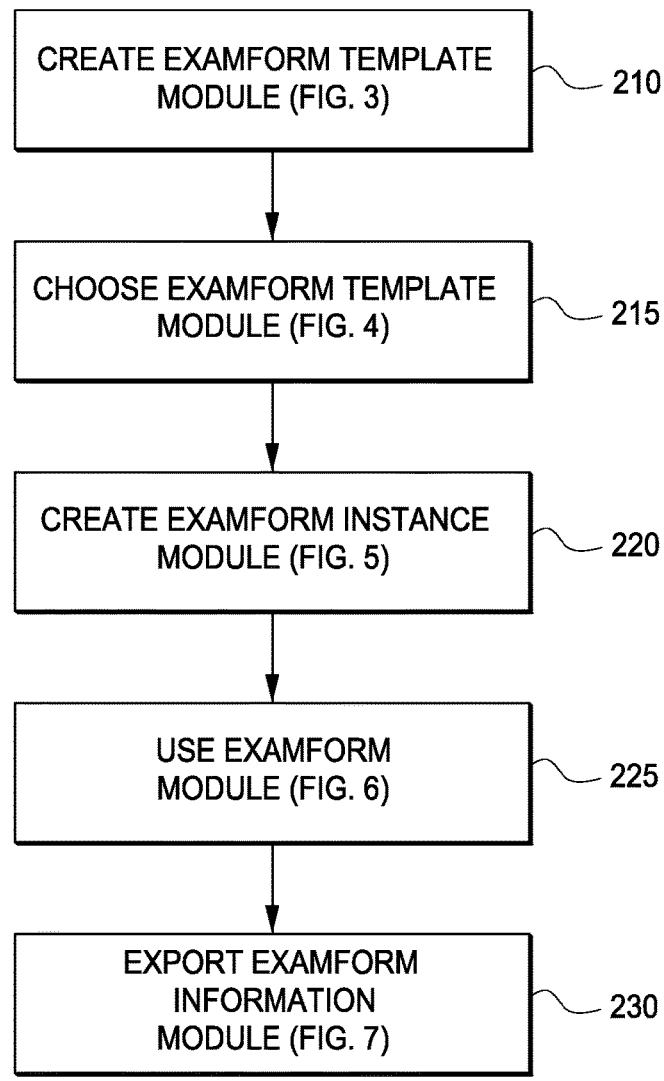
FIG. 2 is a high level flowchart of one example process for using a dynamic medical examination form system such as the one shown in FIG. 1.

FIG. 2 is a high level flowchart of a process by which dynamic medical examination forms may be created according to one or more embodiments. The process shown in FIG. 2 is typically performed by the dynamic medical examination forms software 151, executing on the examination forms computing device 150 (or other computing device). However, one of skill in the art will readily appreciate that the process may be performed by more software distributed across a plurality of systems. In one embodiment, a software application that is installed on the computing system 150 may generate various user interfaces for interfacing with an operator (e.g., a physician or radiologist), and may include multiple software modules that interface with one another, such as a template creation module, template selection module, examination form creation module, and/or examination form export module, which are each described in further detail below. As used herein, the term "medical examination forms software" refers to a software application that includes one or more of the modules discussed herein, and which may be executed on a computing device such as the computing device 150, PACS workstation 138, and/or any number of other computing devices. Depending on the embodiment, the method of FIG. 2 may include fewer or additional blocks and/or may be performed in a different order than is illustrated. For example, in certain embodiments, one or more of the blocks shown in FIG. 2 may not be performed.

Software code for performing the methods described herein, including the methods of FIGS. 2-7, may be executed by examination form computing device 150, the PACS workstation 138, the EMR system 142, the radiology information system 140, and/or any other suitably configured computing device. The software code may be embodied in a computer readable medium configured for reading by a computing device in order to store the software code in one or more memories of the computing device for execution.

The process begins at block 210, where a template creation module is used to dynamically create an examination form template which may be stored in the examination form template database 132. Additional details of the template creation process are provided below in connection with FIG. 3.

The process may then move to block 215, where a user of the medical examination forms software 151 may use the template selection module in order to select a stored template from the examination form template database 132. As will be described in more detail below in connection with FIG. 4, the template selection module allows a user to find which existing examination form template best suits the examination for which they intend to use the form. In some embodiments, the template may be chosen manually by the user.

Alternatively, an automated process may be used to select a dynamic examination form template based on specified criteria. These criteria may include the examination type that will be conducted, medical imaging modality, attributes of the specific type or model of scanner utilized, patient history, prior examinations, clinical information, the clinical indication for the exam, the facility at which the exam is conducted, insurance information, attributes related to people and entities that will receive the results of the examination such as tumor measurements required by clinical studies, attributes of referring/ordering physicians (including general attributes such as specialty as well as preferences related to individual physicians), and attributes related to the user for the form (including general attributes such as specialty or use role, and well as preferences of the specific users).

Once the appropriate template has been selected, automatically, manually or by some combination, an instance of a dynamic medical examination form may then be generated at block 220 based on the selected template. Thus, the instance created from the template is a first view of the form. As discussed above, multiple other views of the form, each potentially importing data from different data sources and/or outputting data to different data destinations, may or may not be implemented. In some embodiments, the medical examination forms software includes an instance creation module that generates the examination form instance which may be used to capture data relating to a specific medical examination of a patient. An exemplary process for generating the examination form instance is discussed in additional detail below in connection with FIG. 5.

Once an instance of the examination form has been created, the process then moves to block 225, where the examination form may be accessed and filled out by an appropriate user. As will be discussed below in connection with FIG. 6, this process may involve manually entering information on the examination form instance, and may additionally involve auto-populating the form with information related to the patient from other devices or systems on the network 205. Once the examination form has been completed, and data has been received or entered into the form, the process then moves to block 230, where the data collected in the view of the examination form may be exported to other systems on the network 205 for archiving or storage.

Figure 3:
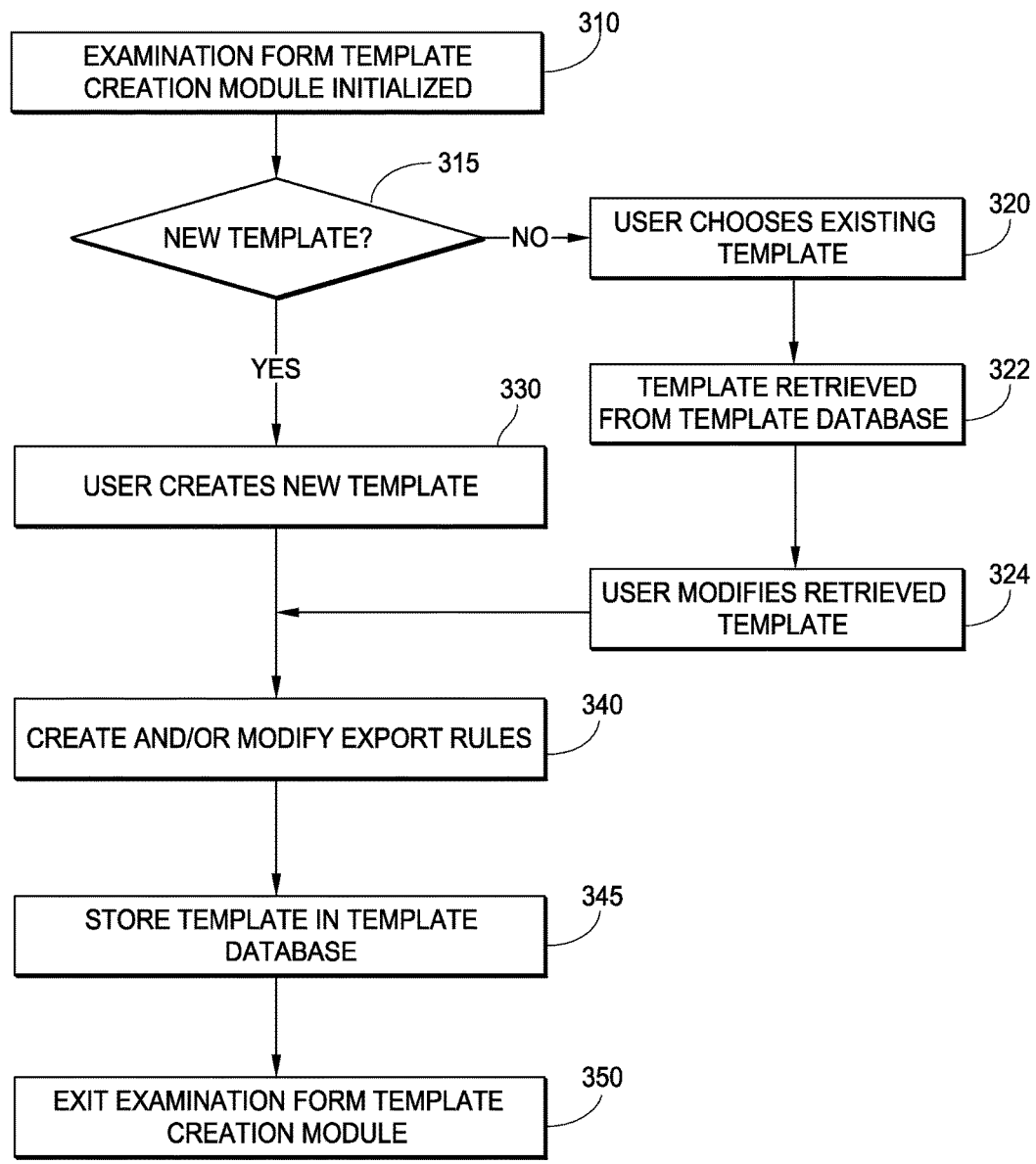
FIG. 3 is a more detailed flowchart illustrating one embodiment of a dynamic medical examination form template creation process.

As discussed above, in certain embodiments, a healthcare professional using the dynamic examination form software 151 may use the software to dynamically create medical examination form templates. Views of electronic examination forms that are used in the course of patient medical examinations may be created using the templates that are created by the examination form template creation module. FIG. 3 is a more detailed flowchart of an exemplary process by which a dynamic medical examination form template may be created. Depending on the embodiment, the method of FIG. 3 may include fewer or additional blocks and/or may be performed in a different order than is illustrated.

The process begins at block 310, where the template creation module is initialized, such as by the user making an appropriate menu selection in a user interface displayed on the computing device 150. The process then moves to decision block 315, where the user is offered a choice as to whether to create an entirely new template, or to create the template out of an already existing examination form template.

If at decision block 315, the user chooses not to create a new template, and instead modify an existing template, the process moves to block 320, where the user chooses an existing template. The existing templates may be presented to the user as a menu choice in which the template description is displayed to the user. In some embodiments, the user may be permitted to display a preview of the content of the templates presented in the menu. Allowing this type of preview helps to ensure a more accurate template choice by the user. Once the user has selected their existing template of choice, the process then moves to block 322, where the selected template is retrieved from the dynamic examination form template database 132, which may be on the PACS database server 130. In other embodiments, examination form templates may be stored local to the computing device (e.g., on a hard drive or optical drive, or available via a LAN) and selectable in block 320. After the selected template has been retrieved, the process then moves to block 324, where the user modifies the selected template according to the current patient examination needs. After the user has modified the selected template, the process then moves to block 340, where examination form export rules are modified. In some embodiments, the existing template selected by the user may already include export rules. In these instances, the user may adopt the existing export rules. Alternatively, the user may modify the already existing export rules to fit the needs of the modified template.

Returning to decision block 315, if the user chooses to create an entirely new dynamic examination form template, the process moves to block 330, where the user constructs an entirely new template. One specific embodiment describing how the user may construct a new template is discussed below in connection with FIG. 8A. Once the new template has been created by the user, the process then moves to block 340 (discussed above), where export rules may be created for the template. Once the export rules have been created, the process then moves to block 345. At block 345, the user may indicate that the template is finished, and the template is stored in the examination form template database 132 (or other database, either local or remote). Once the new template has been stored in one or more databases, the template creation process ends at block 350, and the system exits the examination form template creation module.

Figure 4:
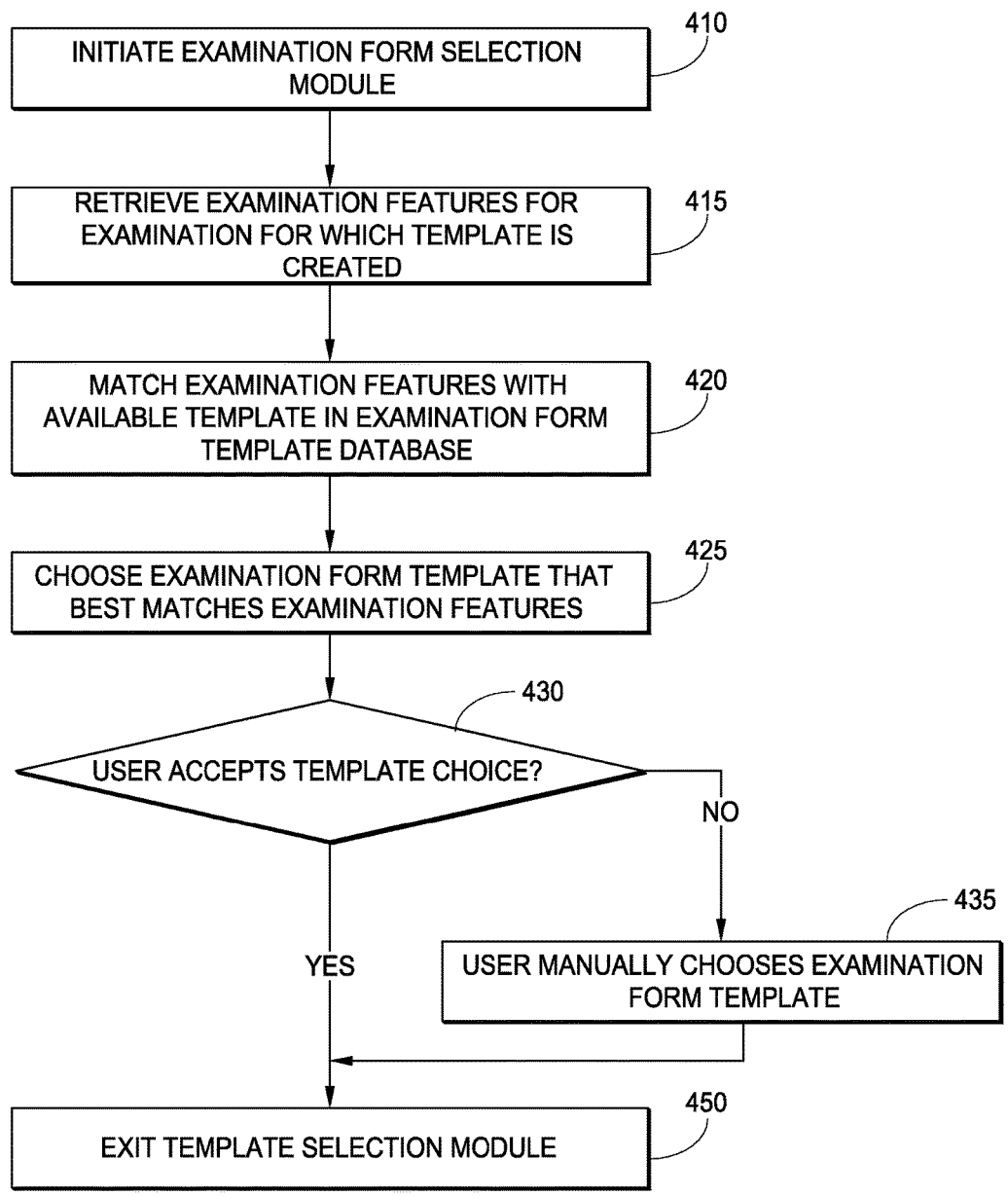
FIG. 4 is a more detailed flowchart illustrating one embodiment of a dynamic medical examination form template selection process.

As discussed above in connection with FIG. 2, users of the dynamic medical examination form software 151 may select an examination form template that suits their needs, or the system may be configured to select a template based on certain criteria. Turning now to FIG. 4, a flowchart provides one example of how a template stored in the template database 132 may be selected for use in a medical examination. In the example shown in FIG. 4, based on information about the examination for which the template will be used, the system attempts to select the appropriate template for the user. If the appropriate template is not found, the user may manually select a template. Depending on the embodiment, the method of FIG. 4 may include fewer or additional blocks and/or may be performed in a different order than is illustrated.

The process begins at block 410 where the template selection module is initialized to receive input from a user. For example, a software module may be called in response to the user making a selection in the examination form software 151 (e.g., via a user interface generated by the software 151 and presented on a display device of the computing device 150) indicating a desire to create a new examination form based on a template. Alternatively, this may occur automatically, for example when a medical examination is performed by technologist or presented for interpretation to radiologist or cardiologist on a PACS workstation. The process next moves to block 415, where the template selection module retrieves examination features related to one or more of the examination to be performed, the user, the location, etc., for which the template will be used The process next moves to block 420, where the retrieved examination features are compared with examination templates stored in the template database 132. Based on that comparison, the template selection module makes an initial selection of the stored template that best fits the retrieved examination features at block 425 and presents that selection to the user.

The process next moves to decision block 430, where the template selection module determines whether the user agrees with the automatic selection, such as by receiving an input from the user indicating such. If the user does not agree with the automatic selection, the process moves to block 435, where the user manually selects a template from which to create the new examination form and the process then moves to block 450 and the template selection module exits. If, however, the user does agree with the automatic selection of a template from the database, the process moves directly to block 450 where the template selection process ends. In one embodiment, the automatic template selection process selects more than one possibly matching template and presents the templates to the user sequentially (e.g., in response to the user indicating that an earlier presented template is not desired) and/or concurrently (e.g., thumbnails of multiple located templates may be displayed to the user).

Figure 5:
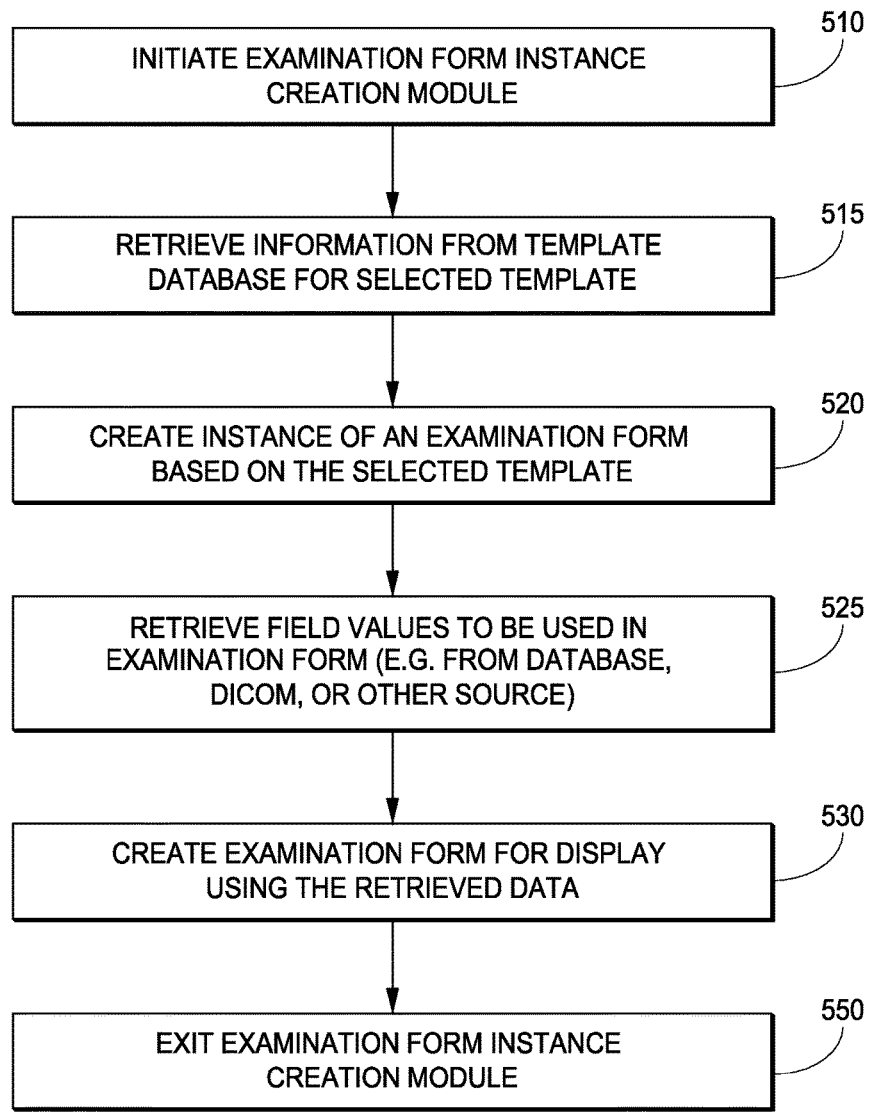
FIG. 5 is a more detailed flowchart illustrating one embodiment of a dynamic medical examination form template instance creation process.

As discussed above in connection with FIG. 2, after a template has been selected for the dynamic medical examination form, an instance (e.g., a first view) of an examination form may be created based on the selected template. FIG. 5 provides a more detailed view of one process of instantiating a dynamic examination form referenced at block 220 of FIG. 2 above. Depending on the embodiment, the method of FIG. 5 may include fewer or additional blocks and/or may be performed in a different order than is illustrated.

The process begins at block 510, where the examination form instance creation module is initiated. Next, the process moves to block 515, where the information from the template selected by the template selection module (or manually by the user) is retrieved from the template database 132. The process then moves to block 520, where an instance of the retrieved examination template is created. The instantiation of the template provides a new examination form that may be used in a patient examination. Once the examination form has been instantiated, the process then moves to block 525, where one or more fields in the examination form may be pre-populated. For example, the fields may be populated by retrieving field values, such as data from the database or DICOM data stored in the PACS system, for example. In some embodiments fields in the examination form may be mapped to specific data stored in these external systems, and the examination form may be configured to automatically retrieve these values. Additional details about the mapping process are discussed below in connection with FIGS. 8 and 9.

Once all of the pre-population data has been retrieved, the process next moves to block 530, where a view of the examination form is generated for display using the retrieved data. The view is displayed to the user so that it may be reviewed, modified, and/or updated based on the results of a subsequent patient examination, for example. Once the view of the examination form has been created and displayed to the user, the examination form instantiation module terminates.

Figure 6:
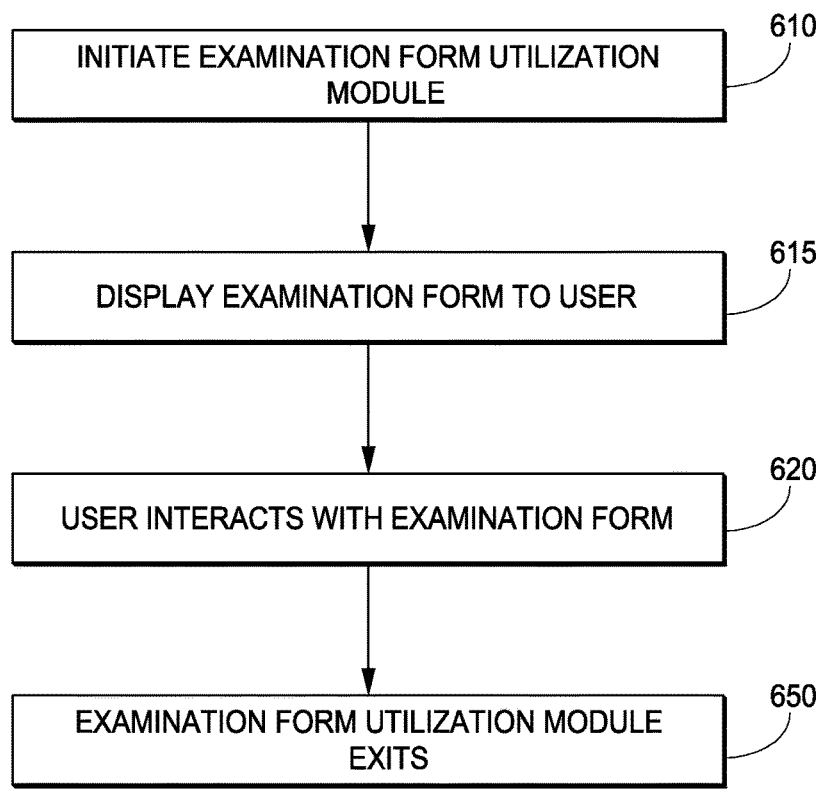
FIG. 6 is a more detailed flowchart illustrating one embodiment of a process for using a selected instance of a dynamic medical examination form.

After completion of the process shown in FIG. 5, a view of the medical examination form has been created and it can be used for collecting data related to a patient medical examination. FIG. 6 is a detailed example of how a dynamic examination form may be used in accordance with one or more embodiments. Depending on the embodiment, the method of FIG. 6 may include fewer or additional blocks and/or may be performed in a different order than is illustrated.

The process begins at block 610, where the examination form utilization module is initiated. Next, in block 615, the selected and instantiated dynamic medical examination form (e.g., the first view of the examination form), including data that has been pre-populated into the form from one or more data sources, is displayed to the user. At block 620, the user interacts with the view of the examination form to enter and/or modify the appropriate data. Use and operation of an exemplary examination form will be discussed in further detail below in connection with FIG. 9.

After the medical examination form has been completed, either manually by a user or automatically, the data entered into the view may then be exported to other systems. By way of example and not of limitation, the data may be exported into a radiology report that may be used by the radiologist. The data may further be exported into an external database, for example, a backup database. Collected data may also be exported to the various other systems on the network 205. These systems may include the PACS, RIS, EMR system or some other clinical information system.

Figure 7:
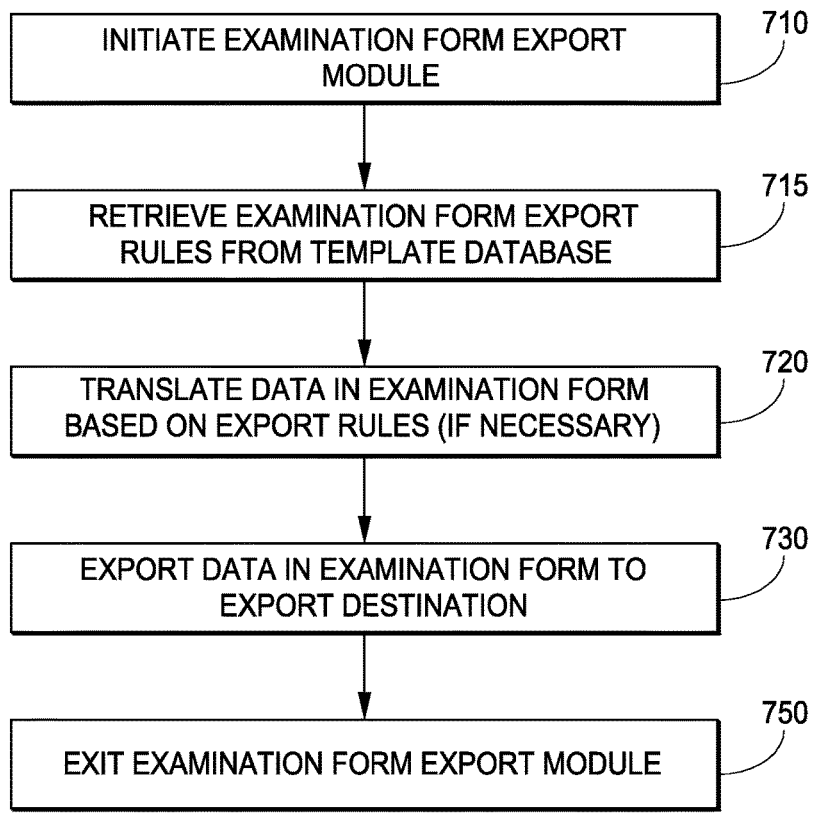
FIG. 7 is more detailed flowchart illustrating one embodiment of a process for exporting information collected in a dynamic medical examination form as shown in FIG. 2.

FIG. 7 is a flowchart providing one example of a process by which information entered into the examination form (e.g., a particular view of an examination form) may be exported to other devices. Depending on the embodiment, the method of FIG. 7 may include fewer or additional blocks and/or may be performed in a different order than is illustrated.

The method begins at block 710, where the examination form export module is initialized. The process then moves to block 715, where the export module retrieves the examination form export rules from the examination form template database 132 (or from another data source in other embodiments). Next, at block 720, data from the examination form is translated into the appropriate format for storage in the external system (if necessary) based on examination export rules retrieved from the template database 132. Once the data has been translated, the data is exported from the examination form to the selected destination system at block 730. When the data has finished exporting, the process ends at block 750 with the export module exiting.

As discussed above with reference to FIGS. 3-6, a user may construct a new template, instantiate that constructed template, and then use the instance of the template to collect and record data related to a patient examination. FIGS. 8A-8E provide an illustration of certain aspects of a graphical user interface environment in which a user may perform these processes according to one or more embodiments.

Figure 8A:
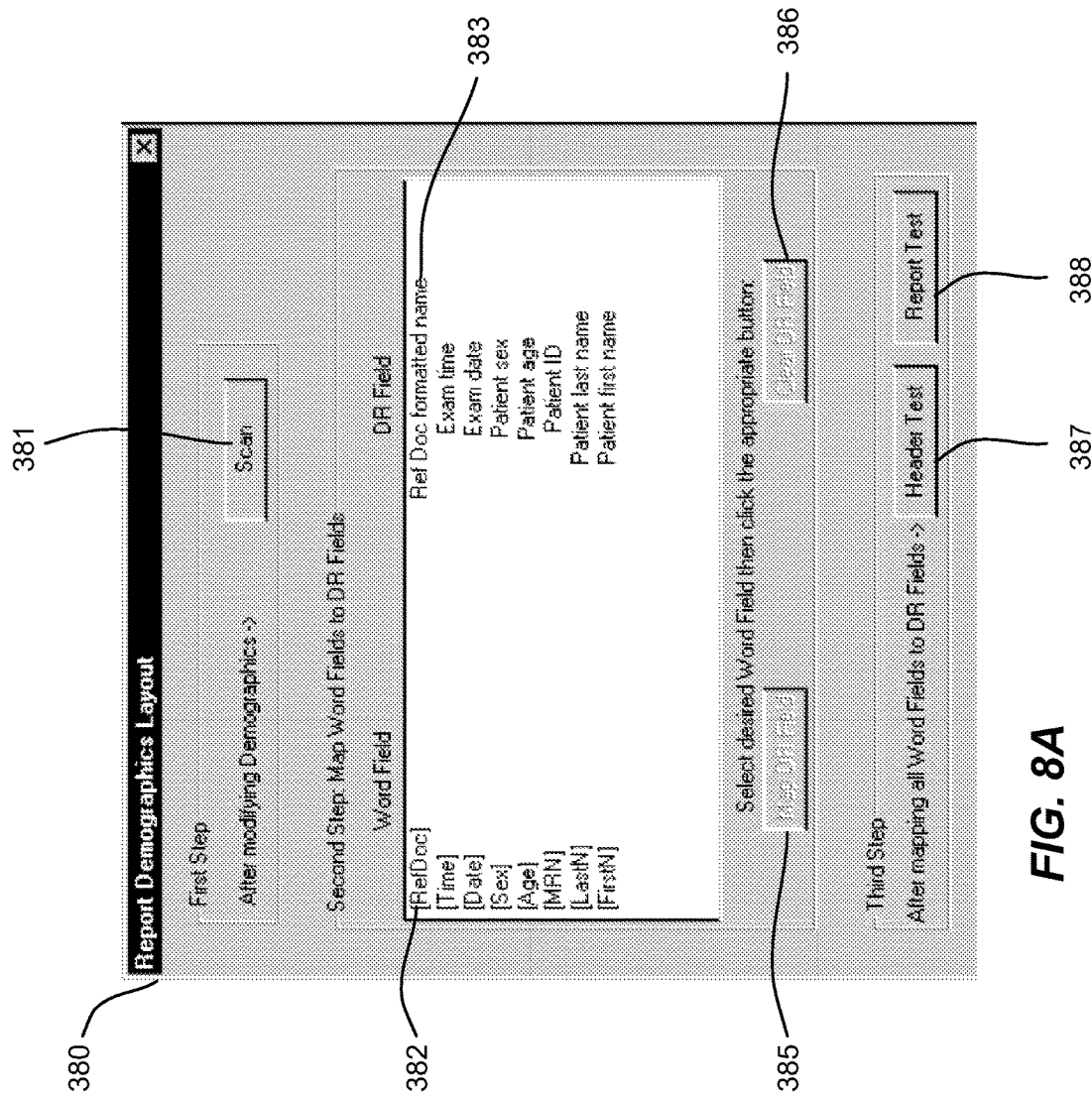
FIGS. 8A-8D are examples of graphical user interfaces which may be provided with dynamic medical examination form software according to one or more embodiments.

With specific reference to FIG. 8A, a graphical user interface generated by a patient management software application, such as the examination forms software 151 of FIG. 1, includes a tab which allows a user to create a new medical examination form using a base template stored in the template database 132, or to create a medical examination form using an already stored template, by modifying and updating the existing template to suit their needs.

As discussed previously, medical examination form templates may be created using the process described in FIG. 3. In some embodiments, the created examination form templates may be configured to interact with or link to external data by default. For example, a template may be configured to map data items in the form template to text and/or image data in a medical data database such as the PACS database 131, for example. The template creator may also designate sections or fields in the template which may be automatically mapped into an external report, such as a reading physician's report that may be created based on the data in the examination form. The template may also be configured to import or pre-populate certain fields with data from external sources. In some embodiments, the examination forms may be uniquely named or associated with a unique identifier, and may be further cross-linked to a specific examination type in order to allow the user to more easily locate the appropriate examination form. By providing these identifying characteristics about the examination form, the system may be configured so that the examination form automatically appears for appropriate users (including, but not limited to, clerical staff, technologists, and reading physicians) when an examination type is selected. In additional embodiments, the medical examination forms may be cross-linked to other items such as a particular facility, an insurance company or type, patient attributes such as age or sex, clinical indications, patient history, and/or some other data item. Based on this cross-linking, appropriate examination forms (one or more) may be presented to a user based on the cross-linked items.

When an examination form is created, it may be configured to contain multiple components and graphical user interface elements, including free text, drop down menus, radio buttons, checkboxes, textboxes, and/or data fields. As noted above, the creator of the medical examination form may designate fields that can be automatically imported from various data sources, such as medical records and/or imaging databases. The creator may also designate examination form fields to be exported to a database or other repository.

By way of example and not of limitation, an examination form may be defined which includes the following text and fields, where a field is indicated by brackets and surrounding text:

Referring Doctor Name: [refdoc]
Time of Exam: [exam time]

In this example, the fields [refdoc] and [exam time] may be mapped to be imported from one or more locations. Alternatively, these fields may have associated mappings which cause their data to be exported to external systems, a database, or other data storage structure. FIG. 8A provides an illustration of a graphical user interface which may be used to create an examination form template with the types of cross-linking and mappings discussed above. In this particular example, a dialog box entitled "Report Demographics Layout" 380 may be displayed as shown after the user has created the initial basic template. The user creating the template may select the scan button 381, which causes the template creation module to identify and list each of the template fields 382 that has been added to the new template. Each of these template fields is shown inside brackets, indicating that it is not actual data, but rather is a data field.

The user may select one of the listed data fields 382. When a data field 382 is selected, the Map External Field button 385 (shown as inactive in FIG. 8A) becomes active, and the user may select the button. Selection of the Map Field button 385 activates an additional dialog box (not shown) that lists each of the data items that is available for import into the examination form. These data elements may be accessed from internal or external data structures. For example, the data elements may be mapped from a PACS data structure or from an external data structure. The user may then select the desired choice for the mapping. Once the user has selected a desired field for the mapping, the mapped field is listed in the same row as a corresponding external data source field 383 for the selected data field 382. In the example shown in FIG. 8A, the [RefDoc] field 382 has been mapped to the "Ref Doc formatted name" data item 383 from the external data source. The user is also provided a Clear external data source field button which allows for the deletion of an association. In some embodiments, a single examination form field may be mapped to more than one external data field. Moreover, a single examination form field may also be mapped to external data fields which exist in multiple external data sources. Once the user is satisfied with their selected and assigned mappings, the user may test the mappings by selecting the header test button 387 which presents an example of the examination form with appropriately mapped and inserted information shown in the appropriate locations.

As noted above, in addition to mapping fields in the examination form template for the purpose of importing data into the form, in some embodiments mappings may also be created in which sections or fields in the examination form can be automatically mapped into one or more external or internal reports, such as a reading physicians report for example. Mapping data collected in an examination form to a physician's reading report may be accomplished using reporting software which allows for the creation of report templates which import data from external data sources. Data contained in any particular examination form can be directed to multiple different destinations. For example, some data might go into a report describing the results of a radiology or cardiology exam. Some data from the same examination form might go into a database stored in the radiology information system, a cardiovascular information system, PACS, a national databank, credentialing organization, or any other local or remote storage device.

In one embodiment, a user can use a report template, and then one can designate where one or more elements of the examination form will automatically appear when a document (report) is opened that is based on the report template that is linked to a particular examination form.

For example, a report template may be created using Microsoft Word®, any other text editor, or a native CDA standard text editor. The report template may be linked to a particular exam type, so that when exams of that type are presented, the report template is used to automatically generate a report document. The report template itself may independently import data from one or more sources, including the examination form linked to that exam type. For example the report template might include the following mappings:

Exam Title: [mapped, for example, from an internal or external data structure]

Date: [mapped, for example, from an internal or external data structure][Exam form contents, indicating one or more specific sections of examination form(s) that are mapped into the report].

The brackets indicates positions in the report template where information can be automatically inserted from one or more of either internal data structures, external data structures, or where information can be inserted from a specified examination form linked to the same examination. The information inserted from the examination form might include one or more lines of text, tables, diagrams, images, or other information. It may include the entire examination form, specified sections of the examination form, or specified fields of the examination form. An examination form that contains drop down menus, checklists, text areas, text fields, checkboxes, or radio buttons may be compiled during this insertion process such that only those items that are selected or completed are imported into the report.

Whether or not information in a medical examination form is mapped to a destination may depend on the content entered into the form. For example, the information in a form may be processed using Natural Language Processing to determine whether the content is mapped and the destination or origination of that mapping. For example, if a specific critical clinical or imaging finding is reported in an examination form data field, the system may automatically generate a "critical results" report, or initiate an e-mail, automated phone call or other similar appropriate action to account for the situation.

Figure 8B:
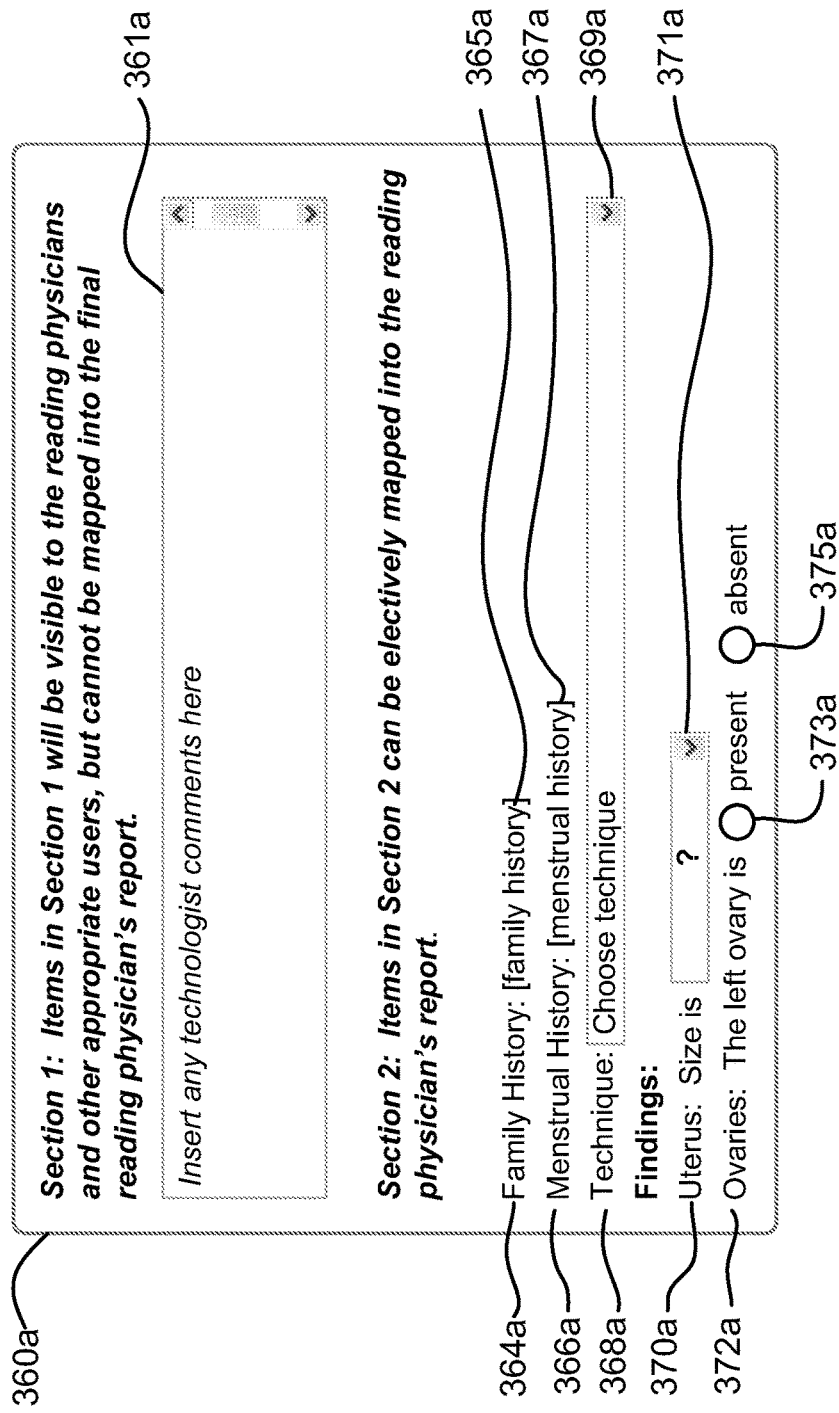

Turning now to FIG. 8B, an example of how data is mapped from a dynamic medical examination form to a report template is provided. As shown, the view 360a of the dynamic medical examination form includes a text box 361a which allows a user (such as a technologist or patient, for example) to enter comments about relevant medical examination. The view 360a also includes a family history field label 364a and a family history input field 365a for input of the patient's family history. This data may already exist in a database or other structure within the PACS system. As a result, this data may be automatically retrieved and populated from the PACS database or other data source, as will be discussed more fully below. The view 360a also includes a menstrual history field label 366a and a menstrual history input field 367a. Additional field labels and fields are also provided such as the technique field label 368a and its corresponding dropdown list 369a; the uterus size field label 370a and its corresponding dropdown list 371a; the ovaries field label and its corresponding radio buttons 373a and 375a.

In this example, view 360a may have data fields that are cross-linked with a reading physicians report (that may be generated at any time in the future) so that the information in Section 2, for example, may be directly mapped into the reading physician's report. In the example shown in FIG. 8B, the family history for the subject patient may already by stored elsewhere in the system, such as in the PACS database, for example. Thus, in addition to exporting data, it is to be appreciated that data may also be imported into the examination form from other sources. For example, in the medical examination form shown in FIG. 8B, the family history data 365a may be imported from an external database, such as an EMR system 142.

Figure 8C:
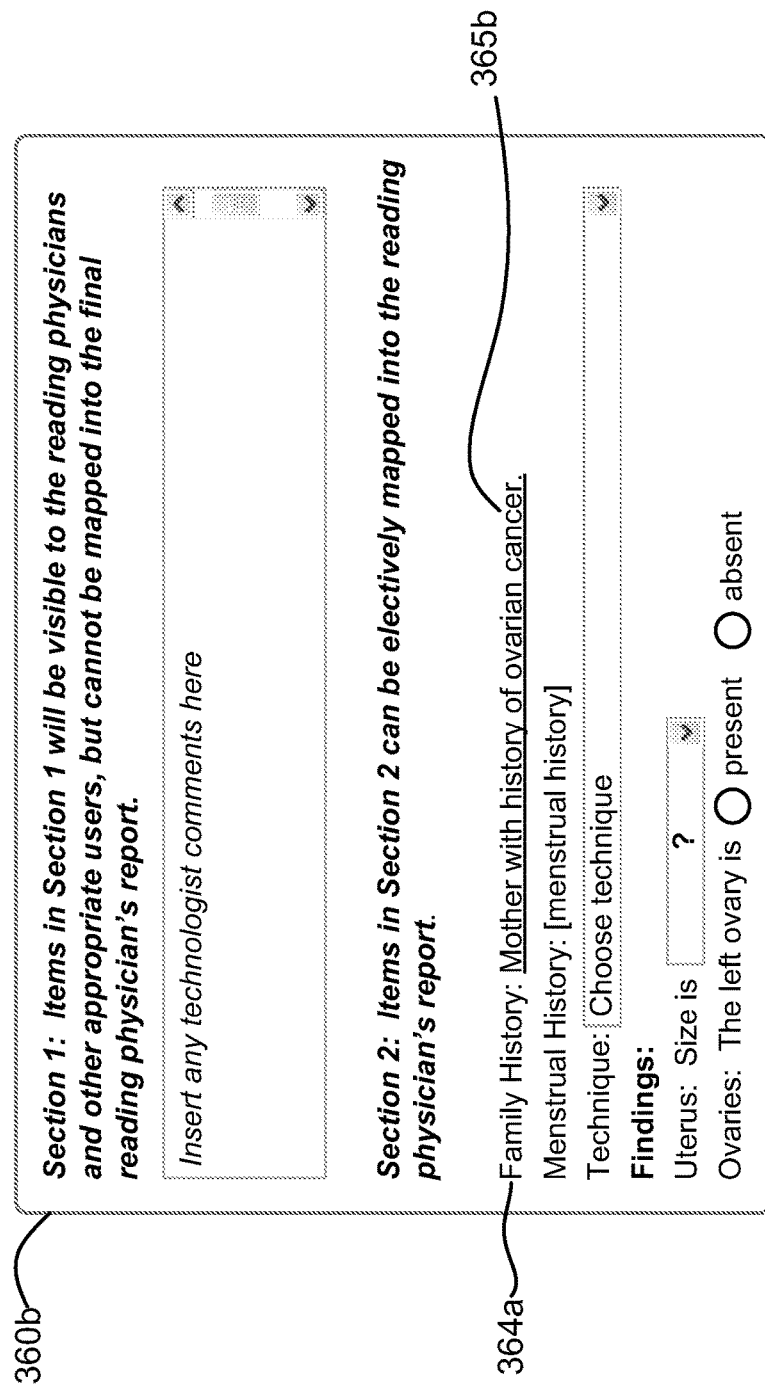
Figure 8D:
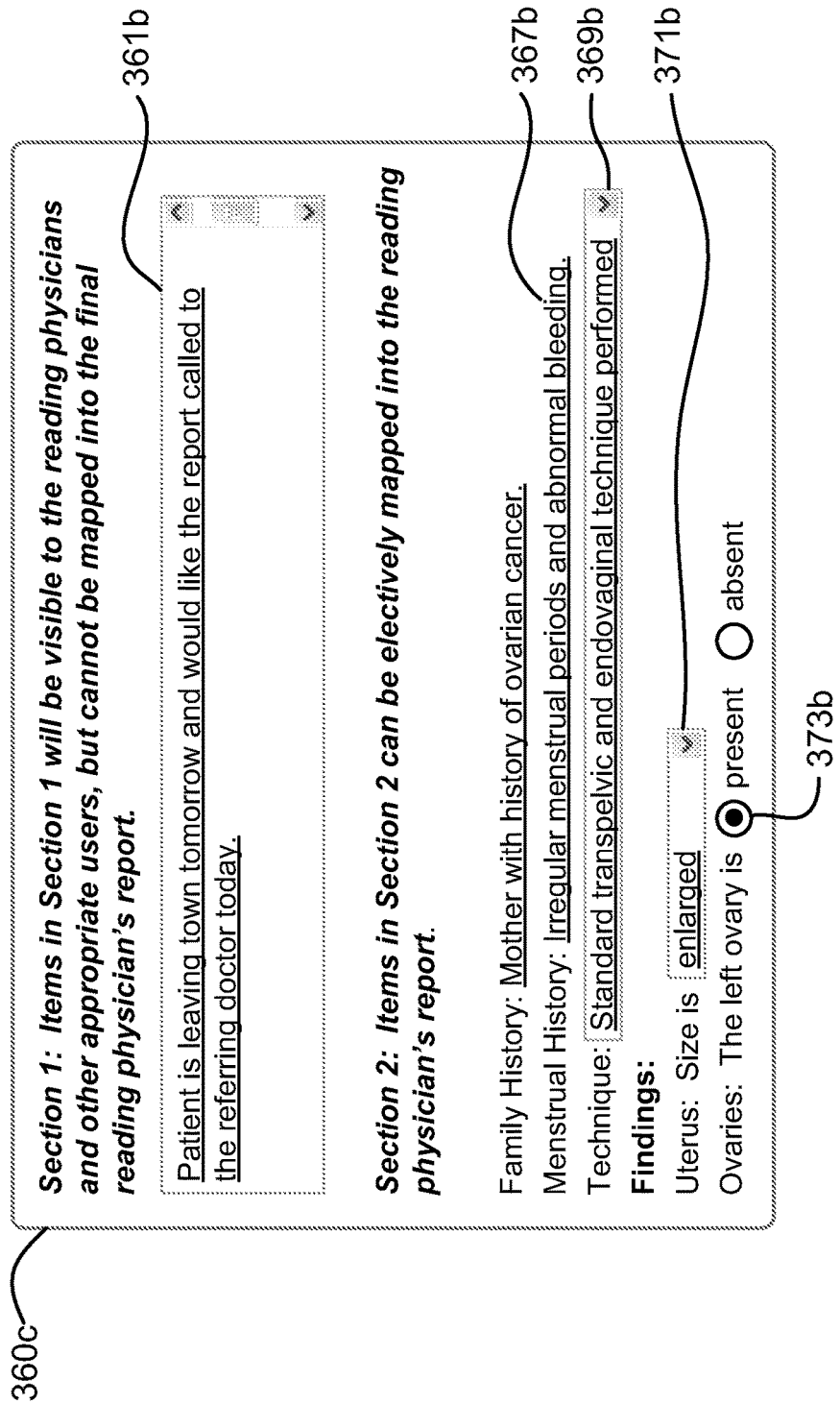

Turning now to FIG. 8C, a view 360b of the medical examination form is shown with the patient history data 365b field having been pre-populated using data retrieved from one or more external systems (and/or entered by a technician, patient, or other user). In one embodiment, a user such as clerical personnel or a technologist with appropriate user rights may see the view 360b. In the example shown, the family history is "Mother with history of ovarian cancer." The retrieved data is displayed as underlined text to show that it is new data that has been added to the form. By providing a visual indication that the data was newly added, the user may be alerted that the veracity of the information may require confirmation. In some embodiments, when a user accesses this view (or any other view) for the first time, the pre-populated data will appear to the user (assuming, of course, that they have sufficient access permissions), and the user may then complete part or all of the remainder of the patient examination form using the user interface elements provided. In the example shown in FIG. 8D, the remaining fields in the view 360b have been completed by a user, as indicated by the underlined text. Once the examination form has been completed, the data entered in the examination form may be mapped to external systems as defined in the examination form template.

In many cases, views of medical examination forms may be completed by a technologist or a clerical employee, and a report using various portions of the data input in the views may be later reviewed by a reading physician. In some embodiments, the medical examination form (or portions of the medical examination form) may be completed by a patient, e.g., at home, in advance of an exam via the web or by some other remote user. Advantageously, the medical examination forms disclosed herein receive information mapped from other sources and map information to targeted data destinations (such as medical reports, quality assurance documents) as part of their initial set up.

A reading physician may display a view of the examination form after various other views of the form have been used to acquire data regarding a specific patient examination. The reading physician may edit the examination form before or after its mapped contents have been transferred to a report. In one embodiment, the physician may execute an action to cause updated contents of the form to be transmitted to the reading physicians report.

The reading physician may further specify preferences which govern how the examination form is displayed when accessed by the reading physician. In some embodiments, the reading physician may specify that the view displayed to the reading physician includes all of the data associated with the examination form. As noted above, certain data fields in an examination form may be cross-linked with data from external systems. For example, an MRI image for a patient may be cross-linked to an examination form, but the image itself is not automatically displayed in the form. Rather, a link to the image (such as a hyperlink to the PACS server, for example) may be provided in the form. In some embodiments, the reading physician may specify a preference that the mapped fields of an examination form are automatically displayed in any report generated from the examination form. For example, the reading physician may specify that any linked images (such as MRI images, for example) be automatically displayed in a report based on the report template for the examination form.

FIG. 8E is an example of a graphical user interface of a report generated by a report template based on the examination form 360 shown in FIGS. 8A-8D. As shown, the some of the data from the examination form 360 has been transferred to the report. The report is typically intended to present information and not to allow information to be modified. As a result, only certain (or all) of the data associated with the examination form (not the dropdown menus and multiple choice selections) are shown in the report. Moreover, that order of information may be different than in the medical examination form, and it might not include all information in the examination form. In addition, some reports may be configured to include information from multiple examination forms to provide additional relevant detail to the reader.

In some embodiments, more dynamic features of the dynamic medical examination forms may be utilized to provide better and more accurate data capture that accounts for changes to a patient's condition over time. In one particular embodiment, medical examination forms may be dynamically created based on a prior examination form (rather than based on an examination form template as described above) so that information from a prior examination may become organically part of the new composite examination form. By making information from the prior examination form available on the new form, the ability to easily compare old findings with new findings is provided. This ability can be helpful to efficiently compare changes in the size of lesions identified in CT, MRI or other scans, without requiring the reader to access multiple files to do so. In another particular embodiment, a medical examination form may be dynamically modified while it is being used. For example, new fields may be added to existing examination forms on the fly in order to document new anomalies (such as new lesions, for example) that were not present in prior examinations, but would need to be following during future examinations. In other embodiments, real-time bidirectional communication between an examination form and some other computer application may be provided to allow for recording correlations of lesion measurements and positions within 2-dimensional images and 3-dimensional imaging volumes.

Figure 9:
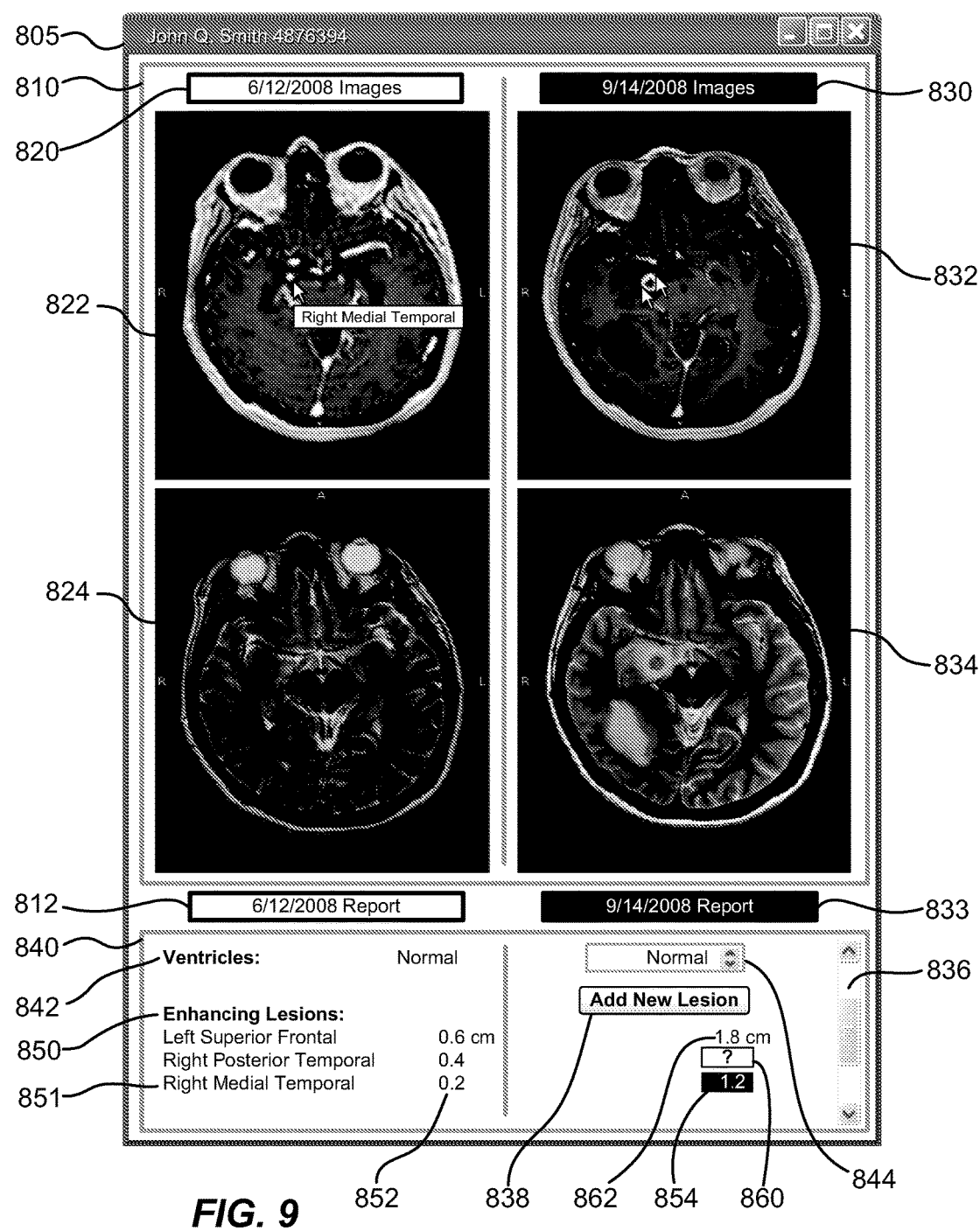
FIG. 9 is a sample graphical user interface illustrating how dynamic medical examination forms may be used in conjunction with external software in accordance with one or more embodiments.

FIG. 9 is an exemplary screenshot of a user interface which illustrates the above-described dynamic embodiments. As shown, the figure includes a screen window 805 which has two regions. The first region 810 (the top ¾ of the drawing) is related to a PACS workstation application, and the second region 840 (the bottom ¼ of the drawing) is related to a view of a patient examination form that has been pre-populated with information from a previous MRI scan of Jun. 12, 2008. The patient data shown in this example is the type of data that may be used by a radiologist to interpret a brain MRI scans in a patient with multiple metastatic brain lesions. However, other types of examinations could also be carried out using the dual region interface 805. For example, in another implementation, an ultrasound technologist may use the interface 805 to document thyroid nodules in a thyroid ultrasound.

In the example provided in FIG. 9, the first region 810 is part of a PACS workstation graphical user interface. The PACS workstation user interface is typically used to interpret medical imaging examinations. As shown, the left column of the first region 810 displays two images 822 and 824 from a patient's prior examination (dated Jun. 12, 2008 in this example) as shown by label 820. The right column of the first region 810 includes two images from follow-up examination (dated Sep. 14, 2008), as shown by label 830.

The second region 840 includes a view of a dynamic examination form having a scroll bar 836 that allows the user to scroll to undisplayed portions. Although the first region 810 and the second region 840 are shown on the same user interface display in this example, it is to be appreciated that the first region and second region can be displayed on separate displays. The second region 840 includes a view of an examination form that was created on Jun. 12, 2008, as shown by label 812. Certain fields used in the prior examination (which took place on Jun. 12, 2008) are replicated on the right side of the second region 840 in order to allow the fields from the old report to be used to allow efficient comparison between the Jun. 12, 2008 examination and the Sep. 14, 2008 examination. In this example, the user would fill in these fields on the right (854, 860, and 862) based on the findings of the corresponding exam on that date.

The right side of the second region 840 of the user interface 805 provides an interface by which a user can enter findings interpreting the images from the first region. Each of the right side and left side of the second region 840 includes data fields for data relating to the corresponding imaging in the first region 810. For example, the "Ventricles" field label 842 is associated with the "Ventricles" field value. For the earlier exam, the Ventricles field value is set to "Normal," while the new examination includes an active dropdown list 844 which allows the user to set the value for the new examination findings. The second region 840 also includes a text label 850 which provides a heading for fields that are listed below.

The fields listed below the text label 850 are related to a series of metastatic lesions identified in the previous medical examination dated Jun. 12, 2008. For example, field label 851 refers to a lesion observed on the "Right Medial Temporal" lobe of the patient. The associated field value 852 lists the size of the lesion as observed in the June examination, "0.2" cm. A corresponding field 854 has been created in the new medical examination form on the right side of the second region 840. In this instance, the user has entered a new value "1.2" cm to reflect a the size of the metastatic lesion on the follow-up exam dated Sep. 14, 2008. This value could be typed in by the user or entered by other means.

In one embodiment, real-time bidirectional communication between the PACS workstation application and the examination form allows for measurements made in the PACS software to be linked to the examination form and entered automatically. In the example shown in FIG. 9, measurements made by the user on the images in region 810 may be immediately translated into values which appear in the measurement fields 854, 860, and 862 in the examination form provided in region 840. For example, the user may click on a measurement field such as measurement field 854, causing the field to become the active field (as indicated by the inverted black/white appearance). The user may then make a measurement of a lesion using the PACS workstation software. In this example, the measurement is performed on the image 832 as indicated by the positioning of two mouse cursors around a lesion near the center of the scan image. The measurement provided by the PACS workstation software is dynamically entered into the active field 854. In one embodiment, this dynamic behavior is provided by a mapping included in the base template for the examination form.

The user interface 805 shown in FIG. 9 also allows the examination forms to be dynamically enhanced to add fields for newly located lesions. In the example provided, an "Add New Lesion" button 838 is provided which allows a user to dynamically create a new lesion field which would specify a location and a measurement. The newly added lesion may be available for subsequent examinations if the new examination form is based on the prior examination form in the same manner as shown in FIG. 9. In additional embodiments, additional user interface elements may be added to account and record additional examination findings that may be tracked in future examinations.

In an additional embodiment, the position where the measurement was taken would be recorded in, for example, in a non-visible portion of the examination form, a database or file. By recording the position of the measurement, the entry in the examination form may be linked to 2-dimensional or 3-dimensional positions in images or image volumes.

In still another embodiment, the bi-directional communication between the examination form software 151 and the external PACS system software may further provide the ability to link examination form fields (such as fields 850) with regions and structures in the images. The linking may be implemented in both directions such that when a user clicks on an examination form field, the corresponding image and specific location in the image may be displayed in the first region 810 of the display 805. Similarly, linking may be implemented from the image to the examination form. In this aspect, when the user moves the mouse cursor over an image displayed in the first region 810, a field associated with the portion of the image under the cursor becomes activated. As illustrated in FIG. 9, the user has positioned the cursor over a portion of image 822 where a measurement has been made and a window labeled "Right Medial Temporal" is automatically displayed, the field name of the measurement made at that position.

FIGS. 10A-10G illustrate additional embodiments in which a graphical user interface environment is provided to allow for medical examination forms to be set up and create, copy, save, modify, and design examination forms. In the examples shown in FIGS. 10A-10G, the dynamic medical examination forms described are referred to as "ExamForms," and it is to be appreciated that these are merely additional embodiments of the dynamic medical examination forms discussed above.

Figure 10A:
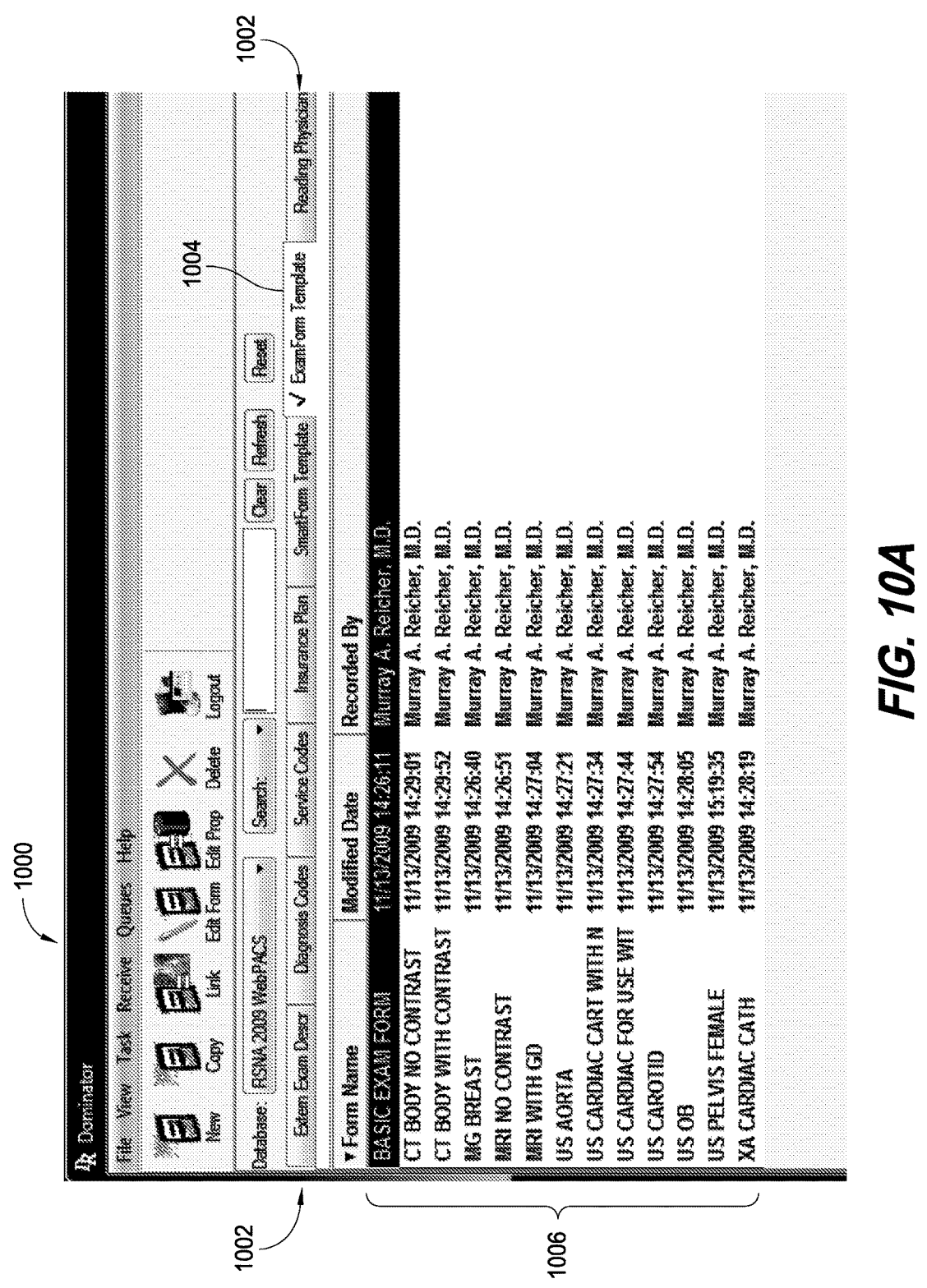

Referring now to FIG. 10A, a user interface 1000 is provided which includes a row of tabs 1002 that may be selected by the user. In some embodiments, the tabs 1002 displayed in the user interface 1002 may be dependent on the identity and/or role of the user. For example, a clerical employee may not have permission to see certain functionality and forms included in the system, in which case, certain tabs may be hidden from that user. A medical doctor, on the other hand, may have extensive permissions within the system, and may therefore be shown additional tabs not presented to other users. As shown the ExamForm Template tab 1004 has been selected by the user, which causes the system to display a list of examination form templates 1006 from which a selection can be made. When the user makes a selection of an examination form template, the user may be taken through a series of template creation screens from which an examination form may be created and linked to specific medical examination types as will be discussed below.

Turning to FIG. 10B, an example of an examination form template editor 1008 which may be presented to a user upon selection of an examination form template from the list 1006 shown in FIG. 10A. The examination form template editor 1008 may include an information window 1010 and an editing window 1012. The information window 1010 may include information that provides instructions to the user in order to assist their design of the examination form. In the example shown in FIG. 10B, the information window 1010 includes step-by-step instructions which provide detailed information to the user for setting up the examination form. The editing window 1012 is used to provide an interface from which the actual design elements of an examination form may be presented and manipulated. In this particular example, multiple sections have been defined which can be associated with different examination form properties and functions. Sections may also be defined based on the identity or role of the user that will complete that specific portion of the examination form. For example, "Section 1" 1014 may be designed so that its contents will be presented to technologists only. The first section 1014 may include various information and fields that may be used by a technologist in an associated patient examination. The first section 1014 may include Technologist Note text area 1018. The Technologist Note area 1018 provides a text area in which a technologist may enter notes regarding their role in a patient examination. The notes entered in this area may be visible to the technologist and to other users having sufficient permissions to access this portion of an examination form created from this template.

In some embodiments, the different sections may also be defined based on whether the information entered into that section of the form will be mapped into an external data entity. For example, in the template shown in FIG. 10B, the first section 1014 may be configured so that none of the information in that section is mapped into the reading physician's report associated with that examination form. In contrast, the information entered into the second section 1016 in an examination form created from the examination form template may be automatically mapped directly into a reading physicians report. For example, the data entered into the exam data fields 1022 may be automatically imported into a precisely mapped location in a physician's report defined for use with this examination form.

As discussed above in connection with FIG. 8A, external data fields may be mapped into an examination form. In the examination template editor interface 1010 shown in FIG. 10B, a number of different patient information fields 1020 are mapped into the examination form. As shown, the patient information fields are indicated by brackets. Mappings to external data may be created using a dialogue box such as that shown in the information window 1010. The information window 1010 provide the user with information on how database fields (indicated by bracketed areas near the top of the ExamForm—arrow) can be created, located, detected and mapped, so that information from an external database (in this example a DR Systems database) or some another datasource can be automatically imported when an ExamForm is created based on this ExamForm template.

Figure 10C:
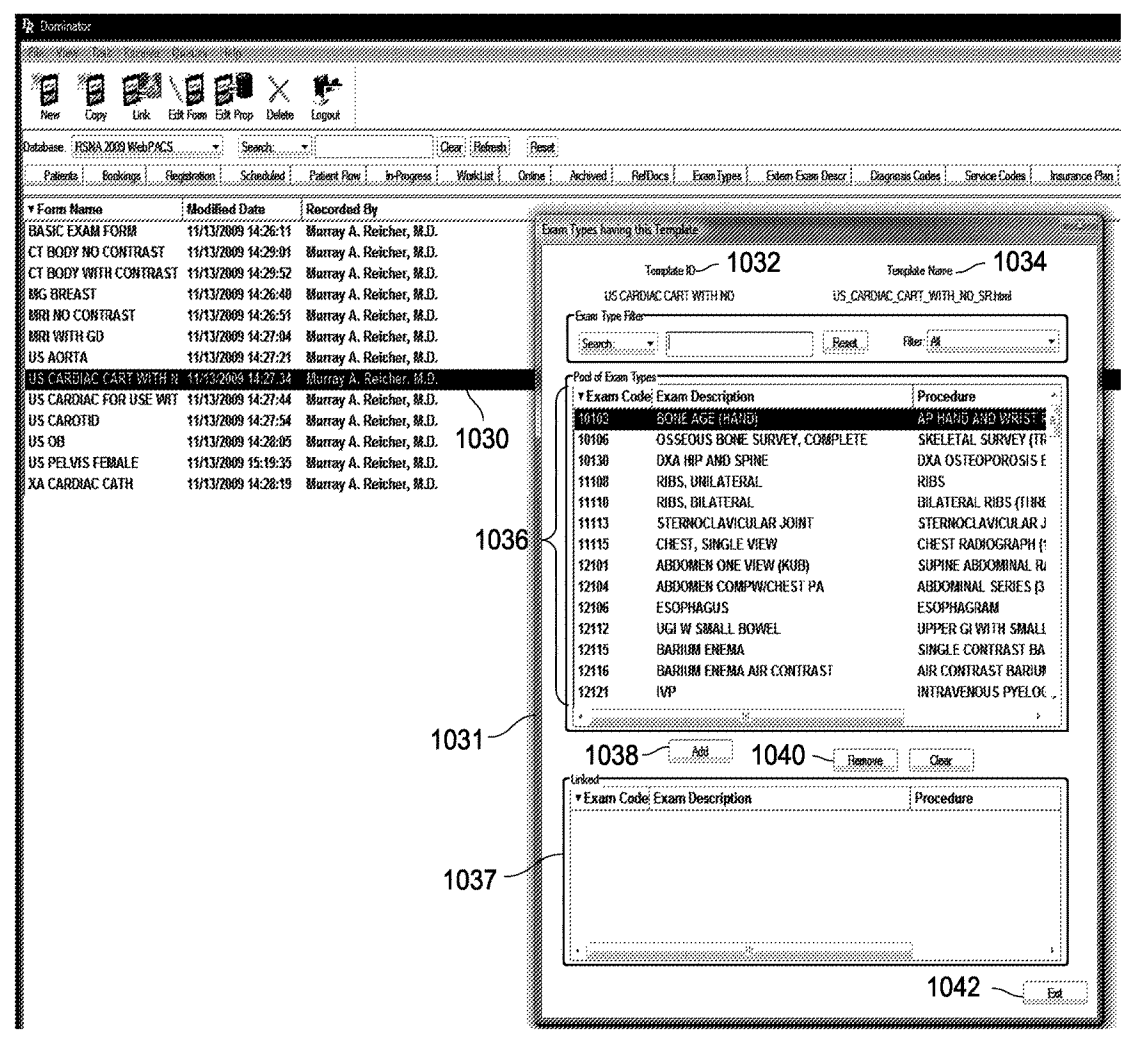

In some embodiments, examination form templates may be linked to one or more specific examination types. When an examination form template is linked to a specific examination type, the appropriate examination form template may be presented to a user when the user wishes to create a new examination form. FIG. 10C is an example of how an examination form template can be linked to one or more specific exam types. Linking an ExamForm template to an exam type is just one of many possible links that can govern which template should be used to create a particular examination form. In the example shown, a user has selected an examination form template 1030 entitled "U S CARDIAC CART WITH NO". In response to that selection, an linking window 1031 is displayed to the user. The linking window 1031 indicates the template with which it is associated by listing a examination template identifier 1032 and an examination template name 1034. A list of medical examinations 1036 from a pool of available examination is presented to the user, from which one or more examinations may be selected for association with the current examination form template. After one or more medical examinations from the list 1036 have been selected, the user may create the link between the examination type and the examination template by selecting the "Add" button 1038. A visual indication of the link is provided by moving the selected examination types from the list 1036 to the linked examination list 1037 below. Links to specific examination types may be removed by selecting the specific examination type and pressing the "Remove" button 1040. Once the user has completed linking the examination types, the window may be closed by selecting the "Exit" button 1042.

As noted above in connection with FIG. 10B, an examination form may be designed such that specific sections of fields may be mapped to other templates, such as reporting templates, for example. FIG. 10D an example of a physician's report template which may be configured to automatically receive data from a corresponding examination form and generate a reading physician's report using data received from, inter alia, an examination form. As shown, a reporting template file name 1050 has been selected by a user. The reporting template may include a mapping 1048 from an examination form which is automatically imported when a physician's report is created based on this report template. The mapping may be created by utilizing the Map to Other Report Dialog box 1054 shown in the figure.

Based on the design of the examination form, some or all of the examination form may be mapped to the physician's report. Furthermore, although this user interface illustrates only one mapping location 1048 for the examination form into the physician's report, various different parts or fields from the examination form may be mapped into different sections of the physicians report. In addition, certain embodiments may provide multiple report templates (and subsequent reports) for the same examination or patient, each with different examination form mappings.

As discussed above in connection with FIG. 8, once an examination form template has been defined, an examination form may be created which is based on the template. FIG. 10E is an example of a view of the examination form that was created from an examination form template. In this particular embodiment, a plurality of data fields 1060 have been automatically imported into the view of the examination form. These data fields 1060 include the patient name, the examination type, the data of birth for the patient, and the date of the examination. The information in the examination report shown in FIG. 10E may be presented to a user to fill assist in completing a patient examination. In this particular example, the first section 1062 includes information about the patient examination which may be presented to a user of the examination form. The user may be a technologist who has been assigned to provide further information into the examination form. The technologist can record comments in the Technologist Note text area 1064 that will be associated with the examination form, but not transmitted to other repositories or physicians' reports in this embodiment.

The second section 1066 of the examination form may provide additional dropdown menus or text fields as shown. Although not shown in this example, many other user interface elements, such as radiobuttons, checkboxes, required fields, etc. can be employed in the examination form design. As noted above, certain data entered into the examination form may be exported to a physicians report. In one embodiment, data is only exported if information is provided by the user. Thus, if no information is placed in the text area next to the Dose-Length Product 1068, when the contents of Section 2 are imported into a physician's reading report, the entire text area will be omitted. In this way, the physician's reading report will not have the appearance of a form, even though it was created, in part, from a form.

Turning now to FIG. 10F, an example of an examination form is provided in which an Auto-Import Note (Section 2) is provided for receiving data from a technologist. In this example, the data may be entered into the examination form while a physician is performing a procedure. Thus, the assistant/technologist can be completing information in the examination form in real-time during the examination procedure. The information entered into the examination form may then be automatically exported into a physicians report, so that the physician need only edit and/or approve the report. As discussed above, some portions of the examination form may be automatically completed when the form is generated. In this example, the information (LEFT HEART CATH, SERVICE CODE 93510) has been automatically imported from a data source. As the procedure is completed, the examination form may be updated to import supplies that were used during procedure.

Figures 1, 10G:
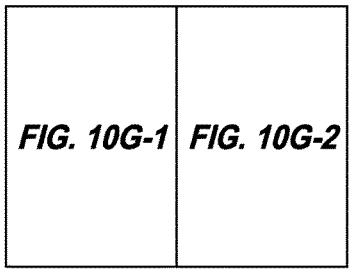
Figures 2, 10G:
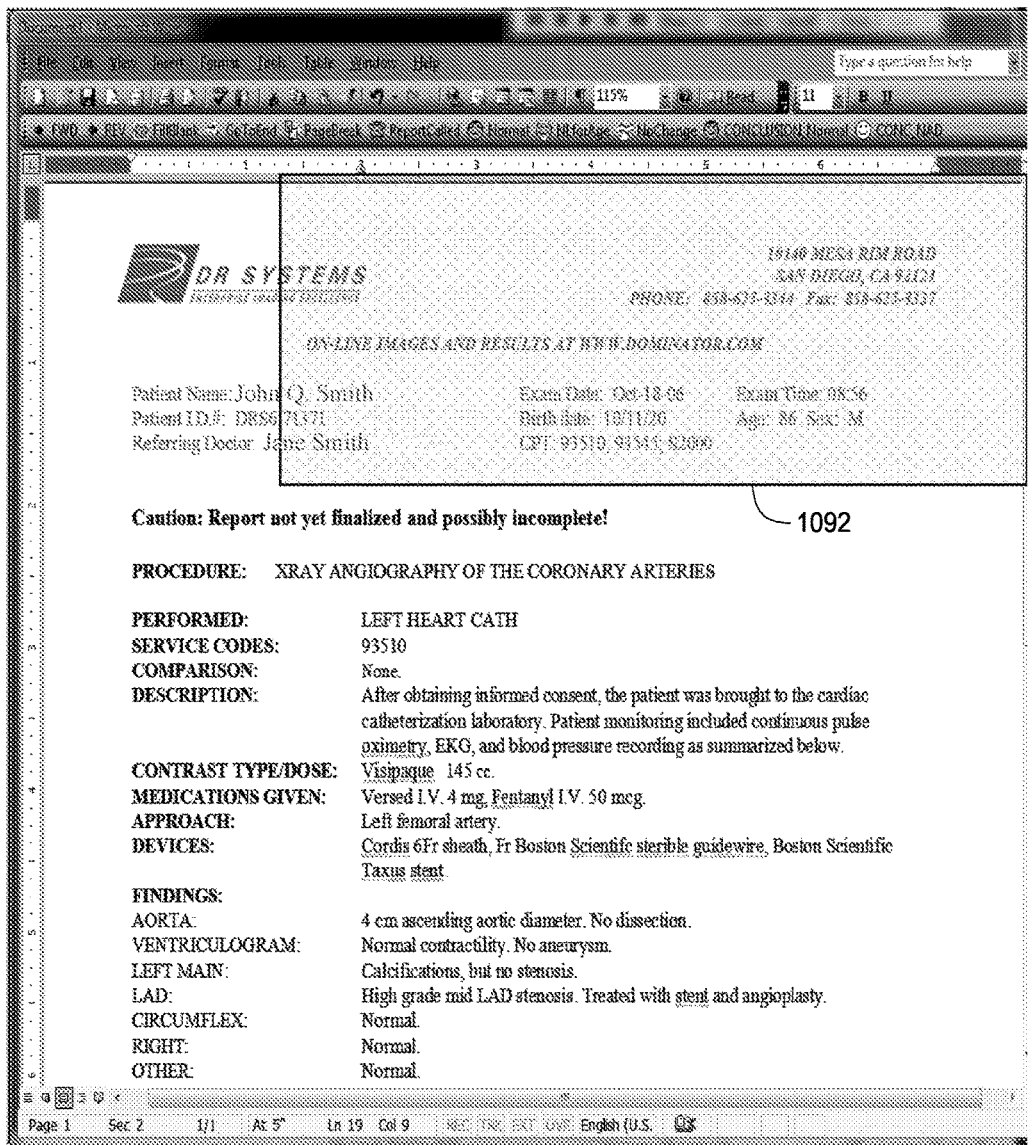

After a technologist has finished using the examination form, a physician's report may be automatically generated to include data exported from the examination form as previously discussed. FIG. 10G is an example of a user interface that a physician may use to evaluate a physician's report. In this example, a completed examination form 1080 is displayed on the left, and the generated physician's report 1090 is displayed on the right. The reading physician may define preferences such that both the examination form 1080 and reading report 1090 are simultaneously displayed. In some embodiments, the physician may be provided extensive control over the timing and location of displayed data. For example, a physician may prefer not to have an examination form displayed at all, but may set his preferences to simply see the physician's report on the right with the examination form mapped data already imported.

In this example, the physician's report 1090 contains information 1092 that did not come from the examination form, but instead came from other data mapping. Depending on the specific implementation, the physician may have the right to edit the physician's report 1090 directly, or may edit the examination form 1080 and then resend the data to the physician's report. In addition, a physician might make various measurements or annotations of associated medical images, with such data transferred automatically to the examination form, the physician's report, both, neither, or other data stores.

Although the specific embodiments set forth above relate to medical examination forms, a skilled artisan will appreciate that the systems and methods disclosed herein may be utilized outside of the medical examination context. For example, the systems and methods could be applied in the context of automotive diagnosis and repair. Other implementation environments are envisioned.

Those of skill will recognize that the various illustrative logical blocks, modules, circuits, and algorithm steps described in connection with the embodiments disclosed herein may be implemented as electronic hardware computer software or combinations of both. To clearly illustrate this interchangeability of hardware and software, various illustrative components, blocks modules, circuits, and steps have been described above generally in terms of their functionality. Whether such functionality is implemented as hardware or software depends upon the particular application and design constraints imposed on the overall system.

Skilled artisans may implement the described functionality in varying ways for each particular application, but such implementation decisions should not be interpreted as causing a departure from the scope of the present invention. The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein.

A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CDROM, or any other form of storage medium known in the art. An exemplary storage medium is coupled to the processor such the processor can read information from and write information to, the storage medium. In the alternative, the storage medium may be integral to the processor. The processor and the storage medium may reside in an ASIC. The ASIC may reside in a user terminal. In the alternative the processor and the storage medium may reside as discrete components in a user terminal.

What is claimed is:

1. A computing system comprising:
    a computer readable storage medium having program instructions embodied therewith; and
    one or more processors configured to execute the program instructions to cause the one or more processors to:
        access a data structure storing an examination form template, wherein the examination form template includes:
            indications of one or more information fields,
            for at least some of the one or more information fields, indications of respective import links to respective data sources that provide information to be automatically imported into respective information fields from the respective data sources, and
            for at least some of the one or more information fields, indications of respective locations within a medical report associated with the examination form template where information input into the respective information field is to be included in the medical report;
        automatically retrieve, based on the indications of the import links of the examination form template, one or more items of information from respective data sources for automatic importation into respective of the at least some of the one or more information fields of the examination form template;
        instantiate an examination form based on the examination form template, the examination form including the one or more information fields of the examination form template and the one or more items of information imported into the respective of the at least some of the one or more information fields of the examination form template;
        in response to a request to view the examination form by a first user:
            determine a first role associated with the first user;
            generate a first interactive view of the examination form for display to the first user based on the first role associated with the first user, wherein the first interactive view is configured to receive data in a first subset of the one or more information fields of the examination form;
            receive data input into at least some of the first subset of the one or more information fields of the first interactive view of the examination form; and
            dynamically store the data input into the at least some of the first subset of the one or more information fields in association with the respective information fields of the examination form;
        generate a medical report based on a portion of the data input into the examination form by the first user, wherein:
            information associated with at least some of the one or more information fields of the examination form is included in the medical report in respective locations as indicated by the examination form template of the examination form, and
            at least some of the information of the examination form is not included in the medical report.

2. The computing system of claim 1, wherein the examination form is associated with a current examination of a patient, and wherein the one or more processors are configured to execute the program instructions to further cause the one or more processors to:
    determine that a previous examination form associated with a previous examination of the patient has previously been generated and includes previous medical information specific to the patient; and
    automatically store at least some of the previous medical information in association with associated information fields of the examination form.

3. The computing system of claim 2, wherein the one or more processors are configured to execute the program instructions to further cause the one or more processors to:
    generate a user interface for display to at least one of the first user or the second user, the user interface including a first one or more medical images from the previous examination of the patient and a second one or more medical images from the current examination of the patient.

4. The computing system of claim 3, wherein the previous medical information includes a measurement of a particular feature depicted in the first one or more medical images and the user interface includes one or more controls configured to allow the at least one of the first user or the second user to provide an updated measurement of the particular feature depicted in the second one or more medical images.

5. The computing system of claim 4, wherein a location of the measurement of the particular feature depicted in the first one or more medical images is stored in the previous examination form.

6. The computing system of claim 5, wherein the one or more processors are configured to execute the program instructions to further cause the one or more processors to:
determine an expected location of the particular feature in the second one or more medical images based at least on the stored location of the measurement of the particular feature.

7. The computing system of claim 3, wherein the one or more processors are configured to execute the program instructions to further cause the one or more processors to:
enable communication between a first software application used to display the first one or more medical images and a second software application used to display the examination form,
wherein the first software application is configured to enable the at least one of the first user or the second user to measure features depicted in the first one or more medical images and/or the second one or more medical images, and the communication between the first software application and the second software application comprises communication of measurements made in the first software application for display in the examination form.

8. The computing system of claim 7, wherein the communication between the first software application and the second software application further comprises:
receiving a selection of a first information field in the examination form generated by the second software application;
receiving a measurement on the first one or more medical images displayed by the first software application; and
automatically populating the first information field in the examination form with the measurement.

9. The computing system of claim 3, wherein the one or more processors are configured to execute the program instructions to further cause the one or more processors to:
access, from the data structure, information associating regions of the second one or more medical images with corresponding information fields of the examination form; and
in response to selection of a particular region of the second one or more medical images, automatically select a particular information field in the examination form that corresponds to the particular region.

10. The computing system of claim 9, wherein the one or more processors are configured to execute the program instructions to further cause the one or more processors to:
in response to automatic selection of the particular information field, automatically populate the particular information field of the examination form with a subsequent measurement on the second one or more medical images.

11. The computing system of claim 3, wherein the one or more processors are configured to execute the program instructions to further cause the one or more processors to:
access, from the data structure, information associating regions of the second one or more medical images with corresponding information fields of the examination form; and
in response to selection of a particular field of the examination form, select a particular region of the second one or more medical images.

12. The computing system of claim 1, wherein the examination form includes one or more user interface controls configured to allow the user to add new information fields to the examination form.

13. The computing system of claim 1, wherein the one or more processors are configured to execute the program instructions to further cause the one or more processors to:
automatically import the one or more items of information into the respective of the at least some of the one or more information fields of the examination form template.

14. The computing system of claim 1, wherein the one or more processors are configured to execute the program instructions to further cause the one or more processors to:
export respective portions of information of the examination form to a plurality of respective data destinations as indicated by one or more export rules of the examination form template, wherein:
not all of the information of the examination form is exported to all of the data destinations as indicated by the export rules such that bandwidth needs are reduced and efficiency of categorizing portions of information of the examination form received at at least some of the data destinations is increased,
at least one of the plurality of respective data destinations is a medical report, and
at least one other of the plurality of respective data destinations is at least one of a billing system, a backup database, a clinical information system, or a data repository.

15. A computer-implemented method comprising:
by one or more processors executing program instructions:
accessing a data structure storing an examination form template, wherein the examination form template includes:
indications of one or more information fields,
for at least some of the one or more information fields, indications of respective import links to respective data sources that provide information to be automatically imported into respective information fields from the respective data sources, and
for at least some of the one or more information fields, indications of respective locations within a medical report associated with the examination form template where information input into the respective information field is to be included in the medical report;
automatically retrieving, based on the indications of the import links of the examination form template, one or more items of information from respective data sources for automatic importation into respective of the at least some of the one or more information fields of the examination form template;
instantiating an examination form based on the examination form template, the examination form including the one or more information fields of the examination form template and the one or more items of information imported into the respective of the at least some of the one or more information fields of the examination form template;

in response to a request to view the examination form by a first user:

determining a first role associated with the first user;

generating a first interactive view of the examination form for display to the first user based on the first role associated with the first user, wherein the first interactive view is configured to receive data in a first subset of the one or more information fields of the examination form;

receiving data input into at least some of the first subset of the one or more information fields of the first interactive view of the examination form; and dynamically storing the data input into the at least some of the first subset of the one or more information fields in association with the respective information fields of the examination form;

generating a medical report based on a portion of the data input into the examination form by the first user, wherein:

information associated with at least some of the one or more information fields of the examination form is included in the medical report in respective locations as indicated by the examination form template of the examination form, and at least some of the information of the examination form is not included in the medical report.

16. A non-transitory computer readable medium storing computer-executable instructions that, when executed by one or more computer processors of a computing system, cause the one or more computer processors to:

access a data structure storing an examination form template, wherein the examination form template includes:

indications of one or more information fields, for at least some of the one or more information fields, indications of respective import links to respective data sources that provide information to be automatically imported into respective information fields from the respective data sources, and for at least some of the one or more information fields, indications of respective locations within a medical report associated with the examination form template where information input into the respective information field is to be included in the medical report;

automatically retrieve, based on the indications of the import links of the examination form template, one or more items of information from respective data sources for automatic importation into respective of the at least some of the one or more information fields of the examination form template;

instantiate an examination form based on the examination form template, the examination form including the one or more information fields of the examination form template and the one or more items of information imported into the respective of the at least some of the one or more information fields of the examination form template;

in response to a request to view the examination form by a first user:

determine a first role associated with the first user;

generate a first interactive view of the examination form for display to the first user based on the first role associated with the first user, wherein the first interactive view is configured to receive data in a first subset of the one or more information fields of the examination form;

receive data input into at least some of the first subset of the one or more information fields of the first interactive view of the examination form; and dynamically store the data input into the at least some of the first subset of the one or more information fields in association with the respective information fields of the examination form;

generate a medical report based on a portion of the data input into the examination form by the first user, wherein:

information associated with at least some of the one or more information fields of the examination form is included in the medical report in respective locations as indicated by the examination form template of the examination form, and at least some of the information of the examination form is not included in the medical report.

* * * * *